United States Patent
Iwato et al.

(10) Patent No.: US 6,958,205 B2
(45) Date of Patent: *Oct. 25, 2005

(54) IMAGE FORMING MATERIAL AND AMMONIUM COMPOUND

(75) Inventors: Kaoru Iwato, Shizuoka-ken (JP); Tadahiro Sorori, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 169 days.

This patent is subject to a terminal disclaimer.

(21) Appl. No.: 10/201,557

(22) Filed: Jul. 24, 2002

(65) Prior Publication Data

US 2003/0143481 A1 Jul. 31, 2003

(30) Foreign Application Priority Data

| Jul. 26, 2001 | (JP) | ................................. 2001-226297 |
| Dec. 27, 2001 | (JP) | ................................. 2001-398047 |

(51) Int. Cl.$^7$ .............................................. G03F 7/004
(52) U.S. Cl. ................................ 430/270.1; 430/271.1; 430/964
(58) Field of Search ................. 430/270.1, 271.1, 430/964

(56) References Cited

U.S. PATENT DOCUMENTS

| 4,696,891 | A |   | 9/1987 | Guzzi |
| 4,792,516 | A |   | 12/1988 | Toriumi et al. |
| 5,525,453 | A |   | 6/1996 | Przybilla et al. |
| 5,731,123 | A |   | 3/1998 | Kawamura et al. |
| 6,060,217 | A |   | 5/2000 | Nguyen et al. |
| 6,083,663 | A | * | 7/2000 | Vermeersch et al. ........ 430/302 |
| 6,117,610 | A |   | 9/2000 | Sheriff et al. |
| 6,153,353 | A |   | 11/2000 | Van Damme et al. |
| 6,352,811 | B1 |   | 3/2002 | Patel et al. |
| 2002/0136979 | A1 |   | 9/2002 | Miyake et al. |
| 2004/0067435 | A1 | * | 4/2004 | Iwato et al. ............. 430/270.1 |

FOREIGN PATENT DOCUMENTS

| EP | 0 899 614 A1 | 3/1999 |
| EP | 0 908 307 A1 | 4/1999 |
| EP | 0 914 964 A2 | 5/1999 |
| EP | 0 945 264 A1 | 9/1999 |
| EP | 0 997 272 A2 | 5/2000 |
| EP | 1 038 668 A2 | 9/2000 |
| EP | 1 059 164 A2 | 12/2000 |
| EP | 1 093 934 A1 | 4/2001 |
| EP | 1 162 063 A2 | 12/2001 |
| EP | 1 162 078 A2 | 12/2001 |
| EP | 1 211 065 A2 | 6/2002 |
| EP | 1 279 519 A2 | 1/2003 |
| EP | 1 400 350 A2 | 3/2004 |
| JP | 07-285275 A | 10/1995 |
| JP | 2002-278050 A | 9/2002 |
| JP | 2003-107688 A | 4/2003 |
| WO | WO 97/39894 A1 | 10/1997 |
| WO | WO 99/11458 A1 | 3/1999 |

OTHER PUBLICATIONS

Robert L. Bentley, et al.; "Syntheses of Heterocyclic Compounds. Part XXXIII. Preparation and Reactions of 4-(2-Dialkylaminophenyl)azetidin-s-ones"; Journal of the Chemical Society, Perkin Transaction 1, 1976, pp. 1725-1734.

* cited by examiner

Primary Examiner—Barbara L. Gilliam
(74) Attorney, Agent, or Firm—Sughrue Mion, PLLC

(57) ABSTRACT

An image forming material includes an image forming layer containing a water-insoluble and alkali-soluble resin, a light-heat converting agent and a compound represented by the following general formula (1). In general formula (1), $R^1$ to $R^3$ independently represent an organic group, where $R^1$ represents a residue forming a ring containing a $N^1$ atom, $R^2$ and $R^3$ may bond to each other to form a ring or at least one of $R^2$ and $R^3$ may bond to $R^1$ to form a ring and $X^-$ represents a conjugate base of an organic acid or inorganic acid. The ring containing the $N^1$ atom is preferably a piperidine ring.

General Formula (1)

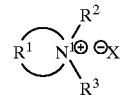

15 Claims, No Drawings

IMAGE FORMING MATERIAL AND AMMONIUM COMPOUND

BACKGROUND OF THE INVENTION

1. Field of the Invention

The present invention relates to an image recording material usable as an offset printing master and a novel ammonium compound used for the recording material, and, particularly, to a positive image forming material useful as a positive planographic printing plate precursor for an infrared laser which planographic printing plate precursor is used for direct plate-making from digital signals from, especially, computers and also to a novel ammonium compound useful for improving the alkali resistance of the image forming material.

2. Description of the Related Art

The recent development of lasers are conspicuous and as, particularly, solid lasers/semiconductor lasers having an emission range from the near infrared region to the infrared region, high-output and small-sized lasers are becoming easily available. These lasers are very useful as exposure light sources when plate-making directly from digital data of computers and the like.

In positive light-sensitive image informing materials for infrared lasers which materials are used for direct plate-making and have long been well-known, novolac resins are used as an aqueous alkali solution-soluble resin. For instance, the positive light-sensitive image forming material disclosed in the publication of Japanese Patent Application Laid-Open (JP-A) No. 7-285275 is a type in which a material which absorbs light to generate heat and a positive light-sensitive compound such as various onium salts and quinonediazide compounds are added to an aqueous alkali solution-soluble resin, such as a novolac resin, having a phenolic hydroxyl group, wherein the positive light-sensitive compound works as a dissolution inhibitor which substantially lowers the solubility of the aqueous alkali solution-soluble resin in image portions and does not eventually manifest the dissolution inhibitive function due to heat in non-image portions, so that the non-image portions are made removable by developing, thereby forming an image.

Also, the positive light-sensitive image forming materials described in WO97/39894 and EP0823327A2 comprise a material which absorbs light to generate heat and a rein which is changed in solubility in an aqueous alkali solution by heat, wherein these image forming materials have low solubility in an aqueous alkali solution in image portions and have increased solubility in an aqueous alkali solution by heat in non-image portions, so that the non-image portions are eventually removable by developing, whereby an image is formed.

In current planographic printing plates, a novolac resin is used particularly preferably from the reasons that there is a large difference in solubility to the developing solution between exposed portions and unexposed portions because it strongly interacts with a dissolution inhibitor and that the resin has high ink-accepting capability. And, with regard to the positive light-sensitive image forming materials for infrared lasers, a novolac resin is also used from the same reasons.

However, a heat mode positive image forming material in exposure using an infrared laser poses the problem that a difference in solubility to the developing solution (dissolution discrimination) between exposed portions and unexposed portions is insufficient and excess developing and developing inferiors are easily caused by variations in working conditions. Also in the case where the surface condition is slightly changed by touching the surface during handling, unexposed portions (image portions) dissolve in a developing solution to leave a scar-wise portion, causing deterioration in printing durability and print-adhesion inferior, leaving fears for affecting various performances such as processing stability, development latitudes and scratching resistance.

SUMMARY OF THE INVENTION

Accordingly, it is an object of the present invention to provide a heat mode positive image forming material having excellent dissolution discrimination and, further to provide an image forming material useful for positive planographic printing plate precursor which resultantly has high latitudes when forming an image by developing, is improved in scratching resistance and enables the formation of a high contrast image.

The inventors of the invention have made studies and as a result, found that the dissolution discrimination can be outstandingly improved by adding a compound represented by the following general formula (1). The present invention was thus completed.

That is, one aspect of the invention provides an image forming material comprising an image forming layer containing a water-insoluble and alkali-soluble resin, a light-heat converting agent and a compound represented by the following general formula (1):

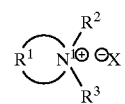

General Formula (1)

wherein $R^1$ to $R^3$ independently represent an organic group, where $R^1$ represents a residue forming a ring containing a $N^1$ atom, $R^2$ and $R^3$ may bond to each other to form a ring or at least one of $R^2$ and $R^3$ bonds to $R^1$ to form a ring and $X^-$ represents a conjugate base of an organic acid or inorganic acid.

The image forming material has a heat mode type image forming layer enabling the formation of an image by irradiation with an infrared laser.

Although the function of the invention is not clear, it is considered that an ammonium compound having such a ring as shown in the general formula (1) manifests strong dissolution inhibitive ability (inhibition) in an alkali-soluble resin due to an electrostatic interaction with the resin, also the $N^+$ atom is concealed sterically due to the ring because of its rigid skeleton during heat mode exposure, the mobility of the molecular side chain is limited, whereby the interaction between the ammonium compound and the binder which interaction has been once dissolved is formed again with difficulty and the inhibition is therefore dissolved efficiently, and eventually the result that the strength of the image portions (unexposed portions) and the excellent solubility of the non-image portions (exposed portions) in the alkali developing solution is made compatible, imparting a very large dissolution discrimination. Also, from this result, it is considered that improvements in development latitudes and scratching resistance are made in practice without lowering sensitivity. This makes it possible to form a high contrast image.

Among the compounds represented by the general formula (1), ammonium compounds represented by the following general formula (1-N) are novel compounds and used particularly preferably for the image forming material of the invention and improve the alkali resistance of the image forming material.

General Formula (1-N)

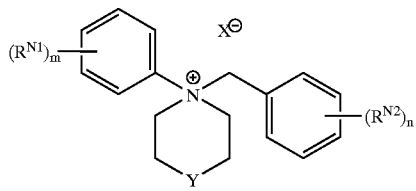

wherein $R^{N1}$ and $R^{N2}$ independently represent a substituent selected from an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a hydroxyl group, a mercapto group, a halogen atom, a cyano group, a sulfo group, a carboxyl group and a nitro group, m and n independently denote an integer from 0 to 5, provided that when plural $R^{N1}$ and $R^{N2}$ are respectively present, plural $R^{N1}$s and $R^{N2}$s may be independently the same or different or may independently bond to each other to form a ring, Y represents —CH$_2$—, —O— or —S— and X$^-$ represents an anion corresponding to a conjugate base of an organic acid or an inorganic acid.

It is to be noted that "heat mode applicable" in the invention means that it is possible to carry out recording by heat mode exposure. The definition of the heat mode exposure in the invention will be described in detail. As described in Hans-Joachim Timpe, IS & Ts NIP 15:1999 International Conference on Digital Printing Technologies. P. 209, it is known that in a process in which a light-absorbing material (e.g., dyes) is photo-exited to form an image through a chemical or physical change in a light-sensitive material, namely in the process from the photo excitation of the light-absorbing material to the chemical or physical change, there are two modes when the process is roughly classified by modes. One of these modes is a so-called photon mode in which the photo-excited light-absorbing material is deactivated by some photochemical interaction (e.g., energy transfer and electron transfer) with other reactive materials in the light-sensitive material, as a result the activated reactive materials cause the chemical or physical change required for the formation of an image. Another is a so-called heat mode in which the photo-exited light-absorbing material generates heat to be deactivated and the reactive materials cause the chemical or physical change required for the formation of an image by utilizing the heat. Although there are, besides the above modes, specific modes such as an ablation mode in which materials are scattered explosively by photo energy collected locally and a multiple photon absorption mode in which one molecule absorbs a large number of photons at a time, these specific modes are omitted here.

Exposure processes making use of the foregoing each mode are referred to as photon mode exposure and heat mode exposure. A technological difference between the photon mode exposure and the heat mode exposure is based on whether or not the amount of energy of a few photons for exposure can be added up in calculating the amount of energy required for an intended reaction. For example, it is supposed to cause some reaction by using n photons. A photochemical interaction is utilized in the photon mode exposure. Therefore, each energy of photons cannot be added up because quantum energy and the law of conservation of momentum. Namely, in order to cause some reaction, the relation "amount of energy of one photon$\geq$amount of reaction energy" must be established. On the other hand, in the heat mode exposure, the amount of energy can be added up because photo energy is converted into heat whose energy can be added up. Therefore, it is only required to establish the relation "amount of energy of n photons$\geq$amount of reaction energy". In this case, the adding-up of the amount of energy is restricted by heat diffusion. That is, if the next photo-excitation-deactivating process starts to generate heat until the heat is dissipated by heat diffusion from the presently focused exposed portion (reaction point), the heat is surely accumulated and added up, leading to a rise in temperature at the portion. However, when the next generation of heat is slow, the heat is dissipated and is not therefore accumulated. Namely, in the heat mode exposure, there is a difference in the result between the case of applying a high energy amount of light for a short time and the case of applying a low energy amount of light for a long time. The former case is more advantageous for the accumulation of heat.

Although in the photon mode exposure, there is the case where a similar phenomenon occurs due to the influence of the diffusion of the following reactive species, such a phenomenon does not occur fundamentally.

That is, in the case of viewing as the characteristics of the light-sensitive material, the intrinsic sensitivity (the amount of energy of the reaction required for the formation of an image) of the light-sensitive material is kept constant to the density of exposure power (w/cm$^2$) (=energy density per unit hour) in the photon mode whereas in the heat mode, the intrinsic sensitivity of the light-sensitive material rises to the density of exposure power resultantly. Accordingly, when in actual, an exposure time of the order making it possible to maintain the productivity required as the image forming material in practice is fixed to compare each mode, sensitization as high as about 0.1 mJ/cm$^2$ can be usually achieved in the photon mode. However, in the photon mode exposure, a reaction is caused no matter how the amount is small, therefore the problem of low exposure fogging is easily caused. On the contrary, in the heat mode exposure, no reaction is caused if the exposure amount is more than a certain level and also, an exposure amount of about 50 mJ/cm$^2$ is usually required in relation to the heat stability of the light-sensitive material; however, the problem of low exposure fogging is avoided.

In the heat mode exposure, in actual, the density of exposure power on the plate surface of the light-sensitive material must be 5000 w/cm$^2$ or more and preferably 10000 w/cm$^2$ or more. However, although no detail is mentioned here, ablation takes place when using a laser with a power density as high as $5.0 \times 10^5$ w/cm$^2$ or more, giving rise to the problems such as contamination of a light source and the use of such a laser is therefore undesirable.

DETAILED DESCRIPTION OF THE PREFERRED EMBODIMENTS

The present invention will be explained in detail.

The image forming material of the invention must comprise an ammonium compound having a ring represented by the general formula (1), an alkali-soluble resin and a light-heat converting agent in an image forming layer. The components constituting the image forming layer will be hereinafter explained one by one.

Compound Represented by the General Formula (1)

$R^1$ to $R^3$ in the general formula (1) independently represent an organic group and $R^1$ represents a residue forming a ring containing a $N^1$ atom. Here, $R^2$ and $R^3$ may bond to each other to form a ring or at least one of $R^2$ and $R^3$ may bond to $R^1$ to form a ring. $X^-$ represents a conjugate base of an organic acid or inorganic acid.

$R^1$ may be any group as far as it is a polyvalent organic group forming a ring containing a $N^1$ atom and may be not only a hydrocarbon type ring, but also a ring containing plural nitrogen atoms or other heteroatom such as an oxygen atom or a sulfur atom. Also, $R^1$ may be a ring having a double bond or those taking a polycyclic structure.

Preferable examples of $R^1$ may include those in which the ring structure to be formed is a three-membered ring to a ten-membered ring. Those having a three-membered ring to an eight-membered ring are preferable in consideration of inhibition-dissolving ability, and those having a five-membered ring or a six-membered ring are preferable in consideration of synthetic aptitude.

The ring containing a $N^1$ atom may have a substituent. Examples of the substituent include an alkyl group, aryl group and halogen atom.

Although $R^2$ and $R^3$ may be optionally selected from whole organic groups, the both are preferably groups such as alkyl groups, aryl groups and the groups represented by the following general formula (2) wherein the sum of the numbers of carbon atoms of the both is 6 or more from the viewpoint of developing the inhibition, namely strong dissolution inhibitive ability. Further, at least one of them preferably has a branched or cyclic structure. Also, at least one of them preferably contains an aromatic ring and it is more preferable that both of $R^2$ and $R^3$ contain aromatic rings.

General Formula (2)

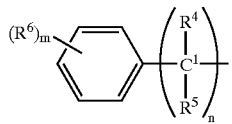

wherein $R^4$, $R^5$ and $R^6$ independently represent any optional substituent which can bond to each other to form a ring, may be the same of different or may form a double bond with the $C^1$ carbon atom, n denotes an integer of either 0 or 1 and m denotes an integer from 0 to 5, when plural $R^6$s are present, they may be the same or different or may bond to each other to form a ring. When n is 1, a structure in which at least either one of $R^4$ and $R^5$ is a hydrogen atom is preferable and a structure in which the both are hydrogen atoms is most preferable from the viewpoint of synthetic aptitude.

Examples of substituents represented by $R^2$ or $R^3$ may include alkyl groups (those having preferably 1 to 20 carbon atoms, more preferably 1 to 16 carbon atoms and particularly preferably 1 to 12 carbon atoms and specific examples include methyl, ethyl, n-butyl, isopropyl, tert-butyl, n-octyl, n-decyl, n-hexadecyl, cyclopropyl, cyclopentyl, cyclohexyl and 2-cyclohexylethyl), alkenyl groups (those having preferably 2 to 20 carbon atoms, more preferably 2 to 12 carbon atoms and particularly preferably 2 to 8 carbon atoms and specific examples include vinyl, allyl, 2-butenyl, 3-pentenyl and 2-cyclohexenylmethyl), alkynyl groups (those having preferably 2 to 20 carbon atoms, more preferably 2 to 12 carbon atoms and particularly preferably 2 to 8 carbon atoms and specific examples include propargyl and 3-pentynyl), aryl groups (those having preferably 6 to 30 carbon atoms, more preferably 6 to 20 carbon atoms and particularly preferably 6 to 12 carbon atoms and specific examples include phenyl, p-methylphenyl and naphthyl); amino groups (those having preferably 0 to 20 carbon atoms, more preferably 0 to 12 carbon atoms and particularly preferably 0 to 6 carbon atoms and specific examples include amino, methylamino, dimethylamino, diethylamino, diphenylamino and dibenzylamino), alkoxy group (those having preferably 1 to 20 carbon atoms, more preferably 1 to 12 carbon atoms and particularly preferably 1 to 8 carbon atoms and specific examples include methoxy, ethoxy and butoxy), aryloxy groups (those having preferably 6 to 20 carbon atoms, more preferably 6 to 16 carbon atoms and particularly preferably 6 to 12 carbon atoms and specific examples include phenyloxy and 2-naphthyloxy); acyl groups (those having preferably 1 to 20 carbon atoms, more preferably 1 to 16 carbon atoms and particularly preferably 1 to 12 carbon atoms and specific examples include acetyl, benzoyl, formyl and pivaloyl), alkoxycarbonyl groups (those having preferably 2 to 20 carbon atoms, more preferably 2 to 16 carbon atoms and particularly preferably 2 to 12 carbon atoms and specific examples include methoxycarbonyl and ethoxycarbonyl), aryloxycarbonyl groups (those having preferably 7 to 20 carbon atoms, more preferably 7 to 16 carbon atoms and particularly preferably 7 to 10 carbon atoms and specific examples include phenyloxycarbonyl), acyloxy groups (those having preferably 2 to 20 carbon atoms, more preferably 2 to 16 carbon atoms and particularly preferably 2 to 10 carbon atoms and specific examples include acetoxy and benzoyloxy), acylamino groups (those having preferably 2 to 20 carbon atoms, more preferably 2 to 16 carbon atoms and particularly preferably 2 to 10 carbon atoms and specific examples include acetylamino and benzoylamino); alkoxycarbonylamino groups (those having preferably 2 to 20 carbon atoms, more preferably 2 to 16 carbon atoms and particularly preferably 2 to 12 carbon atoms and specific examples include methoxycarbonylamino), aryloxycarbonylamino groups (those having preferably 7 to 20 carbon atoms, more preferably 7 to 16 carbon atoms and particularly preferably 7 to 12 carbon atoms and specific examples include phenyloxycarbonylamino), sulfonylamino groups (those having preferably 1 to 20 carbon atoms, more preferably 1 to 16 carbon atoms and particularly preferably 1 to 12 carbon atoms and specific examples include methanesulfonylamino and benzenesulfonylamino) sulfamoyl groups (those having preferably 0 to 20 carbon atoms, more preferably 0 to 16 carbon atoms and particularly preferably 0 to 12 carbon atoms and specific examples include sulfamoyl, methylsulfamoyl, dimethylsulfamoyl and phenylsulfamoyl); carbamoyl groups (those having preferably 1 to 20 carbon atoms, more preferably 1 to 16 carbon atoms and particularly preferably 1 to 12 carbon atoms and specific examples include carbamoyl, methylcarbamoyl, diethylcarbamoyl and phenylcarbamoyl), alkylthio groups (those having preferably 1 to 20 carbon atoms, more preferably 1 to 16 carbon atoms and particularly preferably 1 to 12 carbon atoms and specific examples include methylthio and ethylthio), arylthio groups (those having preferably 6 to 20 carbon atoms, more preferably 6 to 16 carbon atoms and particularly preferably 6 to 12 carbon atoms and specific examples include phenylthio), sulfonyl groups (those having preferably 1 to 20 carbon atoms, more preferably 1 to 16 carbon atoms and particularly preferably 1 to 12 carbon atoms and specific examples include mesyl and tosyl), sulfinyl groups (those having preferably 1 to 20 carbon atoms, more preferably 1 to 16 carbon atoms and particularly preferably 1 to 12 carbon atoms and specific examples include methanesulfinyl and benzenesulfinyl), ureide groups (those having preferably 1 to 20 carbon atoms, more preferably 1 to 16 carbon atoms and particularly preferably 1 to 12 carbon atoms and specific examples include ureide, methylureide and phenylureide); phosphoric acid amide groups (those having preferably 1 to 20 carbon atoms, more preferably 1 to 16 carbon atoms and particularly preferably 1 to 12 carbon atoms and specific examples include diethylamidoaphosphoric acid and phenylamidophosphoric acid), hydroxy groups, mercapto groups, halogen atoms (e.g., a fluorine atom, chlorine atom, bromine atom and iodine atom), cyano groups, sulfo groups, carboxyl groups, nitro groups, hydroxamic acid groups, sulfino groups, hydrazino groups, imino groups, heterocyclic groups (those having preferably 1 to 30 carbon atoms and more preferably 1 to 12 carbon atoms and containing a nitrogen atom, oxygen atom or sulfur atom as a heteroatom and specific examples include imidazolyl, pyridyl, quinolyl, furyl, thienyl, piperidyl, morpholino, benzoxazolyl, benzoimidazolyl, benzothiazolyl, carbazolyl, azepinyl and oxiranyl) and silyl groups (those having preferably 3 to 40 carbon atoms, more preferably 3 to 30 carbon atoms and particularly preferably 3 to 24 carbon atoms and specific examples include trimethylsilyl and triphenylsilyl).

These substituents may be further substituted. Also, when two or more substituents are present, they may be the same or different. Also, they may bond to each other to form a ring if possible.

$R^2$ and $R^3$ are independently preferably an alkyl group, aryl group, alkenyl group, alkynyl group or groups obtained by optionally substituting these groups. Further, the sum of the numbers of carbon atoms of the both is preferably 6 or more, more preferably 8 or more and most preferably 10 or more from the view point of inhibition.

There is no particular limitation to the compound represented by $X^-$ as far as it is a conjugate base of an organic or inorganic acid. $X^-$ may be either a high molecular compound or low molecular compound or may be a polyvalent anion. Examples of these anions may include anions corresponding to an organic acid conjugate base, such as $R^{a1}$—$SO_3^-$, $R^{a1}$—$SO_2^-$, $R^{a1}$—$CO_2^-$, $R^{a1}$—$CS_2^-$, $R^{a1}$—O—$CS_2^-$, $R^{a1}$—S—$CS_2^-$, $R^{a1}$—O—$PO_2^-$, $(R^{a1}$—O$)_2PO_2^-$, $R^{a1}$ $(R^{a1}$—O$)PO_2^-$, $R^{a1}$-$EW^1$-$Z^-$-$EW^2$—$R^{a1}$, $(R^{a1})_4B^-$ and $Ar^xO^-$ or anions corresponding to an inorganic acid conjugate base, such as $F^-$, $Cl^-$, $Br^-$, $I^-$, $PF_6^-$, $BF_4^-$, $SbF_6^-$, $ClO_4^-$, $SO_4^{2-}$, $NO_3^-$, $CO_3^{2-}$, $SCN^-$, $CN^-$, $SiF_6^-$, $FSO_3^-$, $I_3^-$, $Br_3^-$ and $IBr_2^-$, wherein $R^{a1}$ is an organic substituent and represents an alkyl group, an alkenyl group, an alkynyl group, an aryl group, an aralkyl group or groups obtained by substituting these groups. When plural $R^{a1}$s are present in the molecule, they may be selected independently or may bond to each other to form a ring, $EW^1$ and $EW^2$ independently represent an electron attractive group and specific examples thereof may include —SO—, —CO—, —$SO_2$— and —CN—, Z represents —$CR^{z1}$— or —N— ($R^{z1}$ represents a hydrogen atom or a substituent) and $Ar^x$ represents an aryl group.

Preferable examples of of the compounds represented by the general formula (1) may include compounds represented by the general formula (1-a).

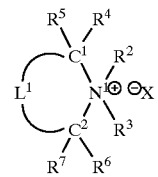

(1-a)

In the general formula (1-a), $R^2$, $R^3$ and $X^-$ respectively have the same meaning as those explained in the general formula (1) and also have the same preferable examples. $R^2$ and $R^3$ independently represent more preferably an alkyl group, an aryl group, an alkenyl group, an alkynyl group or groups obtained by optionally substituting these groups and further, the sum of the numbers of carbon atoms of the both is preferably 6 or more, more preferably 8 or more and most preferably 10 or more from the viewpoint of the inhibition.

Also, $R^4$ to $R^7$ independently represent a hydrogen atom or a substituent. As the substituent, the substituents given as the examples of $R^2$ and $R^3$ in the general formula (1) may be used. $R^4$ to $R^7$ may be the same or different, may bond to each other to form a ring or may bond to $L^1$, $R^2$ and/or $R^3$ to form a ring. Also, in the case where the $C^1$ carbon atom and the $C^2$ carbon atom form a double bond or a triple bond in combination with $L^1$, $R^4$ to $R^7$ may not be present corresponding to this. $L^1$ represents a polyvalent connecting group forming a ring containing —$C^1$—$N^1$—$C^2$— or a single bond. The ring composed of $L^1$, $C^1$, $N^1$ and $C^2$ is preferably a three-membered ring to an ten-membered ring. The ring is more preferably a three-membered ring to a eight-membered ring from the viewpoint of inhibition-dissolving ability and more preferably a five-membered ring and a six-membered ring from the viewpoint of synthetic aptitude.

If two substituents among $R^4$ to $R^7$ bond to the same atom, these two substituents may represent the same atom or substituent and may form a double bond (for example, $R^4$, $R^5$ and $C^1$ may form a carbonyl group —CO— provided that $R^4=R^5=O$).

As more preferable embodiments among the compounds represented by the general formula (1), compounds represented by the general formula (1-b) may be given.

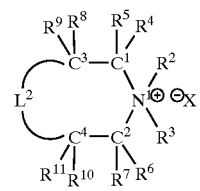

(1-b)

In the general formula (1-b), $R^2$, $R^3$ and $X^-$ respectively have the same meaning as those in the general formula (1) and each preferable examples are also the same. Also, $R^4$ to $R^{11}$ independently represent a hydrogen atom or a substituent. As the substituent, the substituents given as the examples of $R^2$ and $R^3$ in the general formula (1) may be used. $R^4$ to $R^{11}$ may be the same or different, may bond to each other to form a ring or may bond to $L^2$, $R^2$ and/or $R^3$ to form a ring. Also, when the $C^3$ carbon atom and the $C^4$ carbon atom form a double bond or a triple bond in combination with the $C^1$ carbon atom and the $C^2$ carbon atom respectively, when the $C^3$ carbon atom and $C^4$ carbon atom form a double bond or a triple bond in combination with $L^2$ and when $L^2$ represents a double bond connecting the $C^3$ carbon atom with the $C^4$ carbon atom, $R^4$ to $R^{11}$ may not be present corresponding to this.

$L^2$ represents a polyvalent connecting group forming a ring containing —$C^3$—$C^1$—$N^1$—$C^2$—$C^4$— and a single bond or a double bond connecting $C^3$ with $C^4$. Preferable examples of $L^2$ may include those in which the ring to be formed is a five-membered ring to a ten-membered ring. Those having a five-membered ring to an eight-membered ring are preferable from the viewpoint of the inhibition-dissolving ability and those having a five-membered ring or a six-membered ring are preferable in the viewpoint of synthetic aptitude.

When two substituents among $R^4$ to $R^{11}$ bond to the same atom, these two substituents may represent the same atom or substituent and may form a double bond (for example, $R^4$, $R^5$ and $C^1$ may form a carbonyl group —CO— provided that $R^4=R^5=O$).

When two substituents among $R^4$ to $R^{11}$ bond to the adjacent two atoms, these two substituents may represent the same atom or substituent and may form a three-membered ring (for example, $R^4$, $R^8$, $C^1$ and $C^3$ may form an epoxy group provided that $R^4=R^8=O$).

As more preferable embodiments among the compounds represented by the general formula (1), compounds represented by the general formula (1-c) may be given.

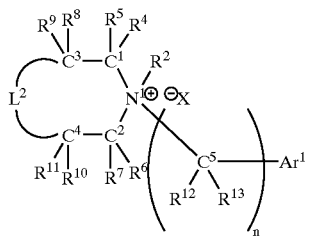

(1-c)

In the general formula (1-c), $R^2$ and $X^-$ respectively have the same meaning as those in the general formula (1) and each preferable range is also the same. $R^2$ is more preferably an alkyl group, an aryl group, an alkenyl group, an alkynyl group or groups obtained by optionally substituting these groups. Further, the number of carbons of $R^2$ is preferably 2 or more, more preferably 3 or more and particularly preferably 4 or more from the viewpoint of the inhibition.

Also, $R^4$ to $R^{13}$ independently represent a hydrogen atom or a substituent. As the substituent, the substituents given as the examples of $R^2$ and $R^3$ in the general formula (1) may be used. $R^4$ to $R^{13}$ may be the same or different, may bond to each other to form a ring or may bond to $L^2$, $R^2$ and/or $R^3$ to form a ring. Also, when the $C^3$ carbon atom and the $C^4$ carbon atom form a double bond or a triple bond in combination with the $C^1$ carbon atom and the $C^2$ carbon atom respectively, when the $C^3$ carbon atom and $C^4$ carbon atom form a double bond or a triple bond in combination with $L^2$ and when $L^2$ represents a double bond connecting the $C^3$ carbon atom with the $C^4$ carbon atom, $R^4$ to $R^{11}$ may not be present corresponding to this.

$Ar^1$ represents an aromatic cyclic group and substituted or unsubstituted phenyl, naphthyl, anthranyl, phenanthrenyl, pyridyl, pyrazyl, imidazolyl, quinolinyl, indolyl, isoquinolinyl, pyrrolyl, furanyl, pyrazolyl, triazolyl, tetrazolyl, oxazolyl, oxadiazolyl, thiazolyl and pyrimidinyl may be used. $Ar^1$ may bond to $L^2$, $R^2$ and $R^4$ to $R^{13}$ to form a ring.

n denotes an integer of 0 or a positive integer and is preferably 0, 1, 2 or 3, more preferably 0, 1 or 2 and particularly preferably 0 or 1. Plural $R^{12}$s and $R^{13}$s are present inevitably when n is 2 or more and plural $R^{12}$s and $R^{13}$s may be respectively the same or different or may independently bond to each other to form a ring.

$L^2$ represents a polyvalent connecting group forming a ring containing —$C^3$—$C^1$—$N^1$—$C^2$—$C^4$— and a single bond or a double bond connecting $C^3$ with $C^4$. Preferable examples of $L^2$ may include those in which the ring to be formed is a five-membered ring to a ten-membered ring. Those having a five-membered ring to an eight-membered ring are preferable from the viewpoint of the inhibition-dissolving ability and those having a five-membered ring or a six-membered ring are preferable in the viewpoint of synthetic aptitude.

When two substituents among $R^4$ to $R^{13}$ bond to the same atom, these two substituents may represent the same atom or substituent and may form a double bond (for example, $R^4$, $R^5$ and $C^1$ may form a carbonyl group —CO— provided that $R^4=R^5=O$)

When two substituents among $R^4$ to $R^{13}$ bond to the adjacent two atoms, these two substituents may represent the same atom or substituent and may form a three-membered ring (for example, $R^4$, $R^8$, $C^1$ and $C^3$ may form an epoxy group provided that $R^4=R^8=O$).

As more preferable embodiments among the compounds represented by the general formula (1), compounds represented by the general formula (1-d) may be given.

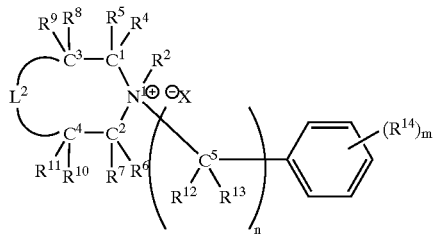

(1-d)

In the general formula (1-d), $R^2$ and $X^-$ respectively have the same meaning as those in the general formula (1) and each preferable range is also the same. $R^2$ is more preferably an alkyl group, an aryl group, an alkenyl group, an alkynyl group or groups obtained by optionally substituting these groups. Further, the number of carbons of $R^2$ is preferably 2 or more, more preferably 3 or more and particularly preferably 4 or more from the viewpoint of the inhibition.

Also, $R^4$ to $R^{14}$ independently represent a hydrogen atom or a substituent. As the substituent, the substituents given as the examples of $R^2$ and $R^3$ in the general formula (1) may be used. $R^4$ to $R^{14}$ may be the same or different, may bond to each other to form a ring or may bond to $L^2$, $R^2$ and/or $R^3$ to form a ring. Also, when the $C^3$ carbon atom and the $C^4$ carbon atom form a double bond or a triple bond in combination with the $C^1$ carbon atom and the $C^2$ carbon atom respectively, when the $C^3$ carbon atom and $C^4$ carbon atom form a double bond or a triple bond in combination with $L^2$ and when $L^2$ represents a double bond connecting the $C^3$ carbon atom with the $C^4$ carbon atom, $R^4$ to $R^{11}$ may not be present corresponding to this.

m denotes an integer from 0 to 5. Plural $R^{14}$s are present when m is 2 or more and plural $R^{14}$s may be the same or different or may bond to each other to form a ring.

n denotes an integer of 0 or a positive integer and is preferably 0, 1, 2 or 3, more preferably 0, 1 or 2 and particularly preferably 0 or 1. Plural $R^{12}$s and $R^{13}$s are present inevitably when n is 2 or more and plural $R^{12}$s and $R^{13}$s may be respectively the same or different or may independently bond to each other to form a ring.

$L^2$ represents a polyvalent connecting group forming a ring containing —$C^3$—$C^1$—$N^1$—$C^2$—$C^4$— and a single bond or a double bond connecting $C^3$ with $C^4$. Preferable examples of $L^2$ may include those in which the ring to be formed is a five-membered ring to a ten-membered ring. Those having a five-membered ring to an eight-membered ring are preferable from the viewpoint of the inhibition-dissolving ability and those having a five-membered ring or a six-membered ring are preferable in the view of synthetic aptitude.

When two substituents among $R^4$ to $R^{14}$ bond to the same atom, these two substituents may represent the same atom or substituent and may form a double bond (for example, $R^4$, $R^5$ and $C^1$ may form a carbonyl group —CO— provided that $R^4$=$R^5$=O).

When two substituents among $R^4$ to $R^{14}$ bond to the adjacent two atoms, these two substituents may represent the same atom or substituent and may form a three-membered ring (for example, $R^4$, $R^8$, $C^1$ and $C^3$ may form an epoxy group provided that $R^4$=$R^8$=O).

As more preferable embodiments among the compounds represented by the general formula (1), the compounds represented by the general formula (1-e) may be given.

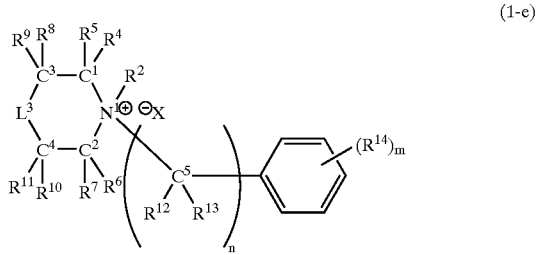

(1-e)

In the general formula (1-e), $R^2$ and $X^-$ respectively have the same meaning as those in the general formula (1) and each preferable range is also the same. $R^2$ is more preferably an alkyl group, an aryl group, an alkenyl group, an alkynyl group or groups obtained by optionally substituting these groups. Further, the number of carbons of $R^2$ is preferably 2 or more, more preferably 3 or more and particularly preferably 4 or more from the viewpoint of the inhibition.

Also, $R^4$ to $R^{14}$ independently represent a hydrogen atom or a substituent. As the substituent, the substituents given as the examples of $R^2$ and $R^3$ in the general formula (1) may be used. $R^4$ to $R^{14}$ may be the same or different, may bond to each other to form a ring or may bond to $L^3$ and/or $R^2$ to form a ring. Also, when the $C^3$ carbon atom and the $C^4$ carbon atom form a double bond or a triple bond in combination with the $C^1$ carbon atom and the $C^2$ carbon atom respectively, when the $C^3$ carbon atom and $C^4$ carbon atom form a double bond or a triple bond in combination with $L^3$ and when $L^3$ represents a double bond connecting the $C^3$ carbon atom with the $C^4$ carbon atom, $R^4$ to $R^{11}$ may not be present corresponding to this.

m denotes an integer from 0 to 5. Plural $R^{14}$s are present when m is 2 or more and plural $R^{14}$s may be the same or different or may bond to each other to form a ring.

n denotes an integer of 0 or a positive integer and is preferably 0, 1, 2 or 3, more preferably 0, 1 or 2 and particularly preferably 0 or 1. Plural $R^{12}$s and $R^{13}$s are present inevitably when n is 2 or more and plural $R^{12}$s and $R^{13}$s may be respectively the same or different or may independently bond to each other to form a ring.

$L^3$ represents a single bond or a double bond connecting $C^3$ with $C^4$ and a polyvalent connecting group forming a ring containing —$C^3$—$C^1$—$N^1$—$C^2$—$C^4$—. As the connecting group, —O—, —S—, —N($R^{L1}$)— or —C($R^{L2}$)($R^{L3}$)— may be used. $R^{L1}$ to $R^{L3}$ may independently represent a hydrogen atom or the substituents given as examples of $R^2$ and $R^3$ in the general formula (1) or may bond to $R^2$ and/or $R^4$ to $R^{14}$ to form a ring structure. $R^{16}$ and $R^{17}$ may be the same or different or may bond to each other to form a ring. When $C^3$ and $C^4$ form a double bond in combination with $L^3$, $R^{L1}$ to $R^{L3}$ may not be present.

When two substituents among $R^4$ to $R^{14}$ and among $R^{L1}$ to $R^{L3}$ bond to the same atom, these two substituents may represent the same atom or substituent and may form a double bond (for example, $R^4$, $R^5$ and $C^1$ may form a carbonyl group —CO— provided that $R^4$=$R^5$=O).

When two substituents among $R^4$ to $R^{14}$ and among $R^{L1}$ to $R^{L3}$ bond to the adjacent two atoms, these two substituents may represent the same atom or substituent and may form a three-membered ring (for example, $R^4$, $R^8$, $C^1$ and $C^3$ may form an epoxy group provided that $R^4$=$R^8$=O).

As more preferable embodiments among the compounds represented by the general formula (1), the compounds represented by the general formula (1-f) may be given.

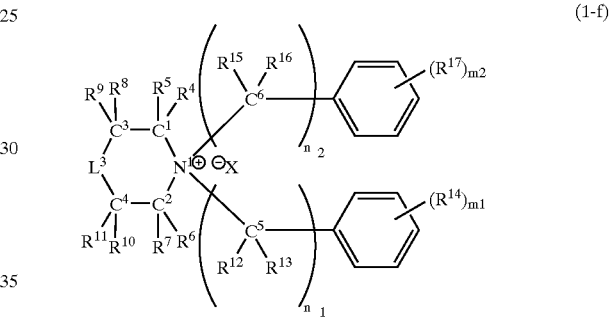

(1-f)

In the general formula (1-f), $X^-$ respectively has the same meaning as that in the general formula (1) and its preferable range is also the same.

Also, $R^4$ to $R^{17}$ independently represent a hydrogen atom or a substituent. As the substituent, the substituents given as the examples of $R^2$ and $R^3$ in the general formula (1) may be used. $R^4$ to $R^{17}$ may be the same or different, may bond to each other to form a ring or may bond to $L^3$, $R^2$ and/or $R^3$ to form a ring. Also, when the $C^3$ carbon atom and the $C^4$ carbon atom form a double bond or a triple bond in combination with the $C^1$ carbon atom and the $C^2$ carbon atom respectively, when the $C^3$ carbon atom and $C^4$ carbon atom form a double bond or a triple bond in combination with $L^3$ and when $L^3$ represents a double bond connecting the $C^3$ carbon atom with the $C^4$ carbon atom, $R^4$ to $R^{11}$ may not be present corresponding to this.

$m^1$ and $m^2$ independently denote an integer from 0 to 5. Plural $R^{14}$s and $R^{17}$s are present when $m^1$ and $m^2$ are independently 2 or more and plural $R^{14}$s and $R^{17}$s may be respectively the same or different or may independently bond to each other to form a ring.

$n^1$ and $n^2$ independently denote an integer of 0 or a positive integer and are preferably 0, 1, 2 or 3, more preferably 0, 1 or 2 and particularly preferably 0 or 1. Plural $R^{12}$s, $R^{13}$s, $R^{15}$s and $R^{16}$s are present inevitably when $n^1$ and $n^2$ are independently 2 or more and plural $R^{12}$s, $R^{13}$s, $R^{15}$s and $R^{16}$s may be respectively the same or different or may independently bond to each other to form a ring.

$L^3$ represents a single bond or a double bond connecting $C^3$ with $C^4$ and a polyvalent connecting group forming a ring containing —C³—C¹—N¹—C²—C⁴—. As the connecting group, —O—, —S—, —N(R$^{L1}$)— or —C(R$^{L2}$)(R$^{L3}$)— may be used. R$^{L1}$ to R$^{L3}$ may independently represent a hydrogen atom or the substituents given as examples of R² and R³ in the general formula (1) or may bond to R² and/or R⁴ to R¹⁴ to form a ring. R¹⁶ and R¹⁷ may be the same or different and may bond to each other to form a ring. When C³ and C⁴ form a double bond in combination with L³, R$^{L1}$ to R$^{L3}$ may not be present.

When two substituents among R⁴ to R¹⁷ and among R$^{L1}$ to R$^{L3}$ bond to the same atom, these two substituents may represent the same atom or substituent and may form a double bond (for example, R⁴, R⁵ and C¹ may form a carbonyl group —CO— provided that R⁴=R⁵=O).

When two substituents among R⁴ to R¹⁷ and among R$^{L1}$ to R$^{L3}$ bond to the adjacent two atoms, these two substituents may represent the same atom or substituent and may form a three-membered ring (for example, R⁴, R⁸, C¹ and C³ may form an epoxy group provided that R⁴=R⁸=O).

Specific examples of the compound represented by the general formula (1) and preferably used in the invention will be hereinafter shown. The compound used in the invention may be optionally selected from the following compounds but the invention is not limited to the exemplified compounds.

The compounds represented by the compounds No. I-1 to I-61 are examples in which the ring containing a N atom is six-membered ring, the compounds represented by the compounds No. II-1 to II-17 are examples in which the ring containing a N atom is five-membered ring, the compounds represented by the compounds No. III-1 to III-17 are examples in which the ring containing a N atom is six-membered ring having a methyl group as a substituent and the compounds represented by the compounds No. IV-1 to IV-17 are examples in which the ring containing a N atom and an O atom is six-membered ring.

| Compound No. | R² | R³ | X⁻ |
|---|---|---|---|
| I-1 | H₃C—CH₂—CH₂—CH₂—CH₂— | phenyl | I⁻ |
| I-2 | C₆H₅—CH₂— | phenyl | Br⁻ |
| I-3 | H₃C—C₆H₄—CH₂— | phenyl | Br⁻ |
| I-4 | O₂N—C₆H₄—CH₂— | phenyl | Br⁻ |
| I-5 | C₆H₅—C(=O)—CH₂— | phenyl | Br⁻ |
| I-6 | C₆H₅—CH₂— | phenyl | PF₆⁻ |
| I-7 | C₆H₅—CH₂— | phenyl | TsO⁻ |
| I-8 | H₃C—C₆H₄—CH₂— | phenyl | BF₄⁻ |

-continued
| | | | |
|---|---|---|---|
| I-9 | 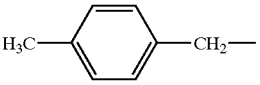 | 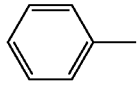 | TsO⁻ |
| I-10 | 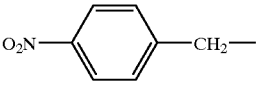 | 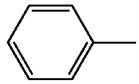 | PF₆⁻ |
| I-11 | 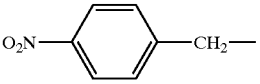 | 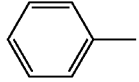 | TsO⁻ |
| I-12 | 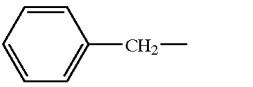 | 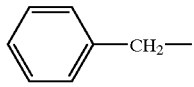 | Br⁻ |
| I-13 | 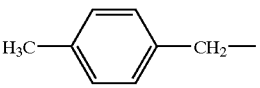 | 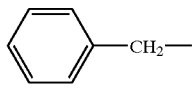 | Br⁻ |
| I-14 | 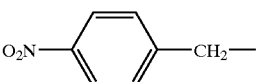 | 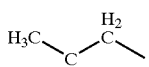 | PF₆⁻ |
| I-15 | 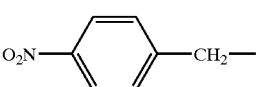 | 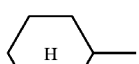 | TsO⁻ |
| I-16 |  | 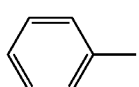 | PF₆⁻ |
| I-17 |  | 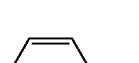 | TsO⁻ |
| I-18 |  | 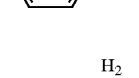 | PF₆⁻ |
| I-19 | 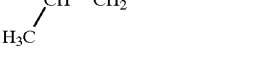 | 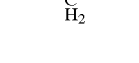 | TsO⁻ |
| I-20 | 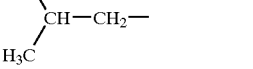 | 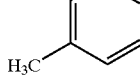 | TsO⁻ |
| I-21 | 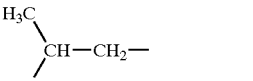 | 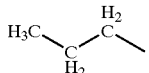 | TsO⁻ |
| I-22 | 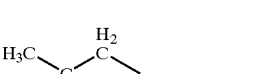 | 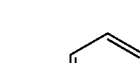 | TsO⁻ |

-continued
| | | | |
|---|---|---|---|
| I-23 | 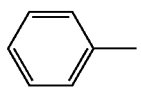 | 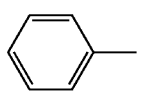 | TsO⁻ |
| I-24 | | | PF₆⁻ |
| I-25 | 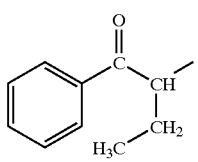 | | TsO⁻ |
| I-26 | 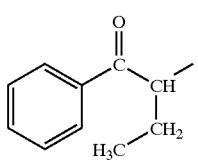 | 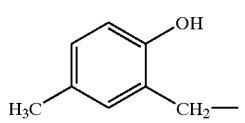 | TsO⁻ |
| I-27 | 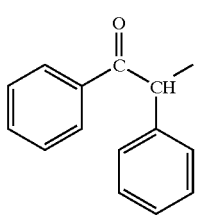 | 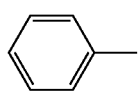 | TsO⁻ |
| I-28 | 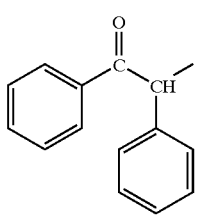 | 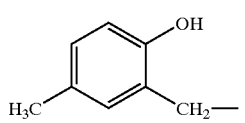 | TsO⁻ |
| I-29 | 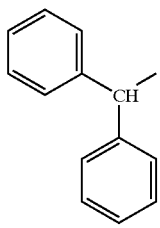 | 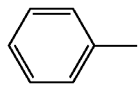 | TsO⁻ |
| I-30 | 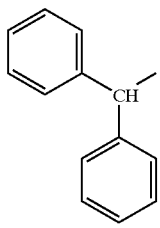 | 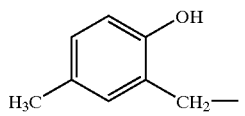 | TsO⁻ |
| I-31 | 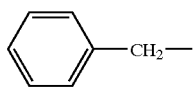 | 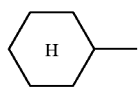 | TsO⁻ |

-continued
| | | | |
|---|---|---|---|
| I-32 | 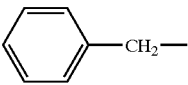 | 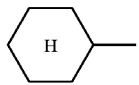 | Br⁻ |
| I-33 | 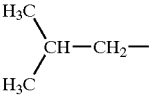 | 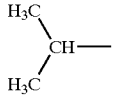 | TsO⁻ |
| I-34 | 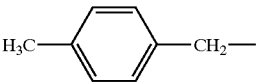 | 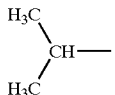 | TsO⁻ |
| I-35 | 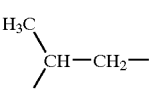 | 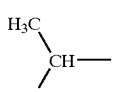 | BF₄⁻ |
| I-35 | 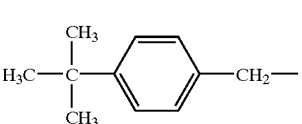 | 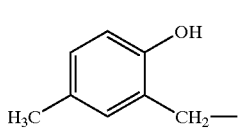 | TsO⁻ |
| I-36 | 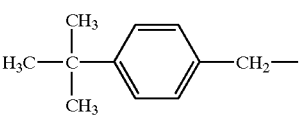 | 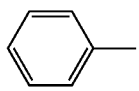 | BF₄⁻ |
| I-37 | 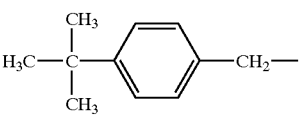 | 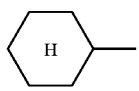 | Br⁻ |
| I-38 | 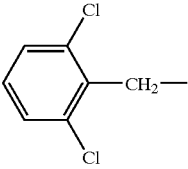 | 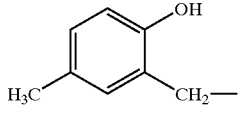 | Br⁻ |
| I-39 | 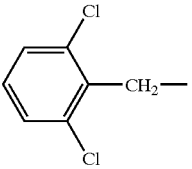 | 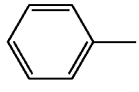 | Br⁻ |
| I-40 | 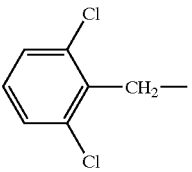 | 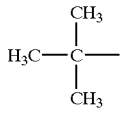 | TsO⁻ |
| I-41 | 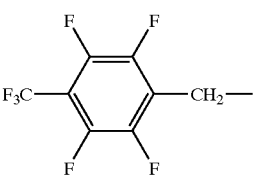 | 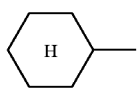 | TsO⁻ |

-continued
| | | | |
|---|---|---|---|
| I-42 | 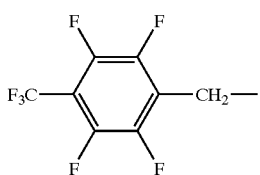 | 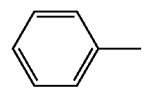 | Br$^-$ |
| I-43 | 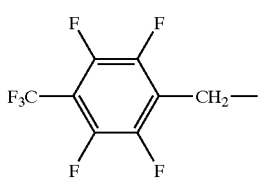 | 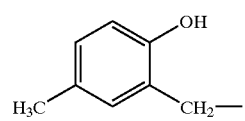 | Br$^-$ |
| I-44 | 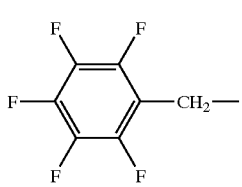 | 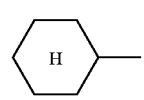 | PF$_6^-$ |
| I-45 | 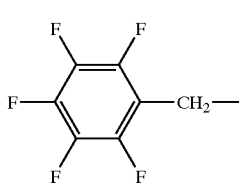 | 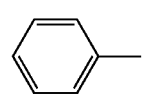 | BF$_4^-$ |
| I-46 | 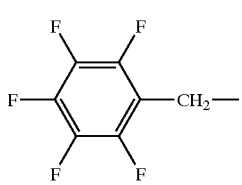 | 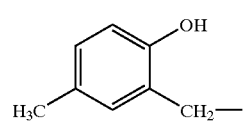 | TsO$^-$ |
| I-47 | 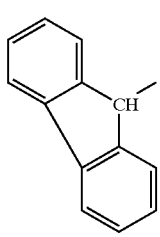 | 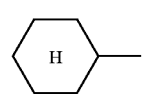 | Br$^-$ |
| I-48 |  | 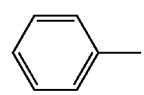 | PF$_6^-$ |
| I-49 | 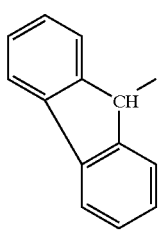 | 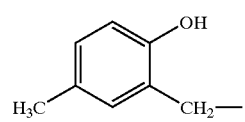 | Br$^-$ |

-continued
| | | | |
|---|---|---|---|
| I-50 | 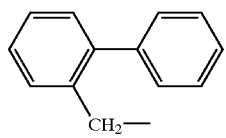 | 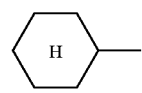 | TsO⁻ |
| I-51 | 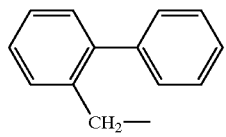 | 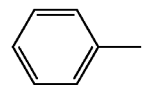 | TsO⁻ |
| I-52 | 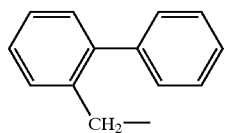 | 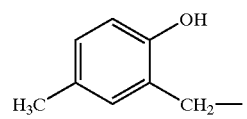 | PF₆⁻ |
| I-53 | 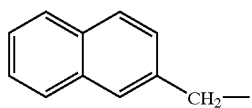 | 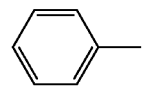 | Br⁻ |
| I-54 | 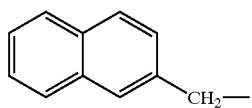 | 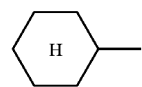 | Br⁻ |
| I-55 | 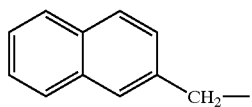 | 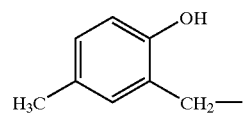 | TsO⁻ |
| I-56 | 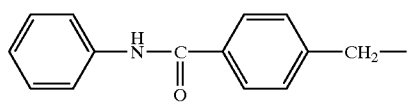 | 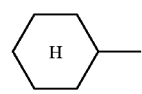 | PF₆⁻ |
| I-57 | 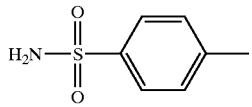 | 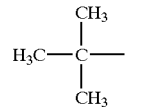 | Br⁻ |
| I-58 | 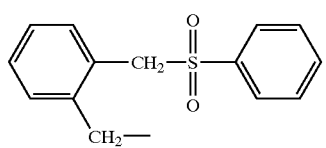 | 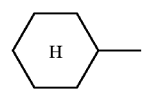 | TsO⁻ |
| I-59 | 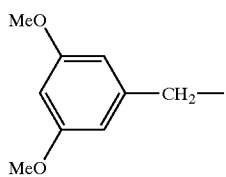 | 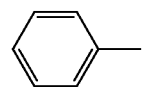 | PF₆⁻ |
| I-60 | 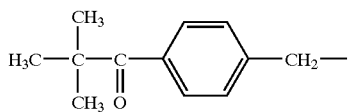 | 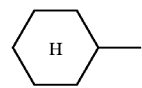 | Br⁻ |

-continued
| | | | |
|---|---|---|---|
| I-61 | 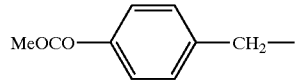 | 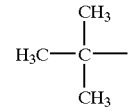 | TsO⁻ |
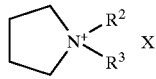
| Compound No. | $R^2$ | $R^3$ | $X^-$ |
|---|---|---|---|
| II-1 | 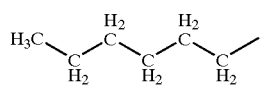 | 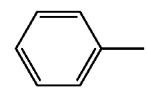 | I⁻ |
| II-2 | 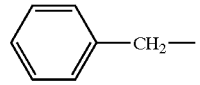 | 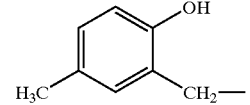 | $PF_6^-$ |
| II-3 |  | 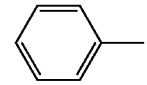 | Br⁻ |
| II-4 |  | 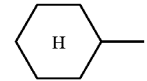 | Br⁻ |
| II-5 | 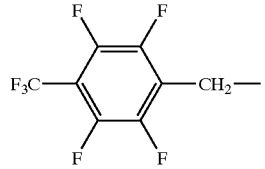 | 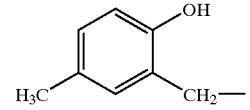 | Br⁻ |
| II-6 | 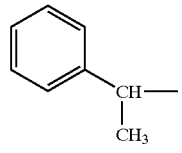 | 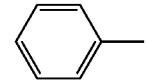 | $PF_6^-$ |
| II-7 |  | 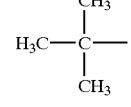 | Br⁻ |
| II-8 | 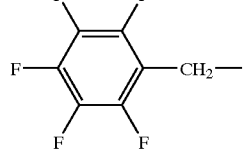 | 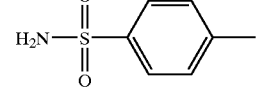 | TsO⁻ |
| II-9 | 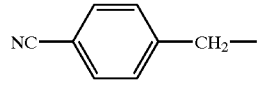 | 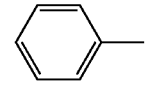 | Br⁻ |

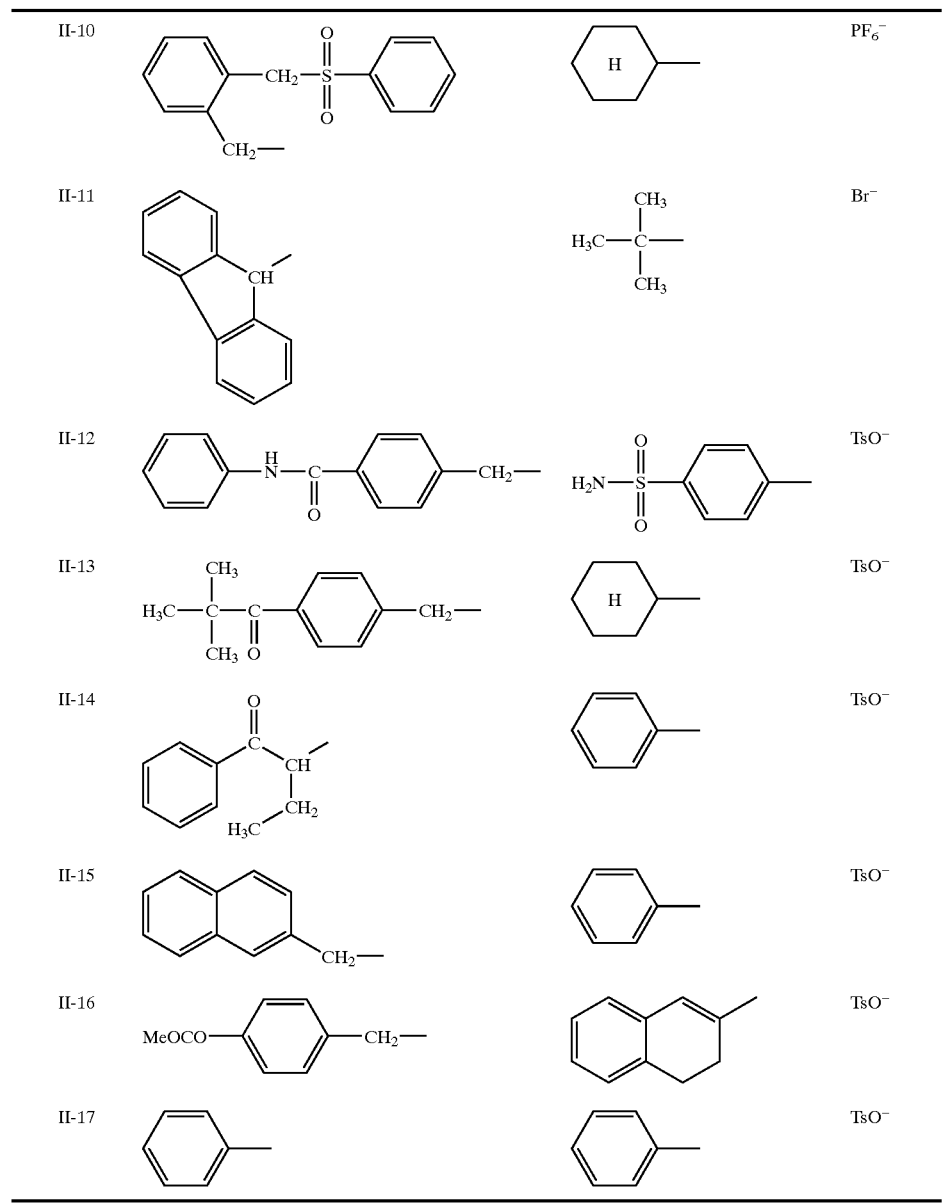
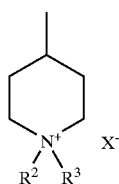
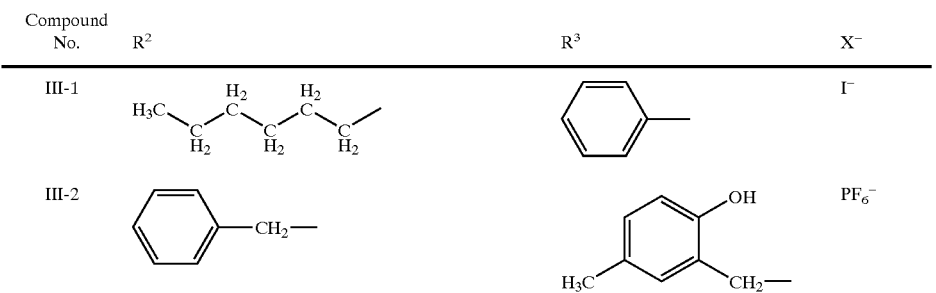

-continued
| | | | |
|---|---|---|---|
| III-3 | 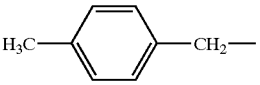 | 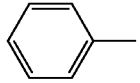 | Br⁻ |
| III-4 | 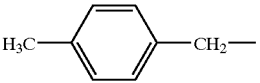 | 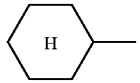 | Br⁻ |
| III-5 | 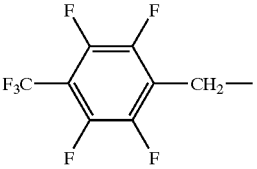 | 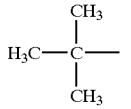 | Br⁻ |
| III-6 | 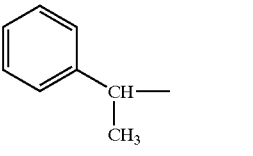 | 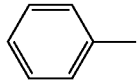 | PF$_6^-$ |
| III-7 | 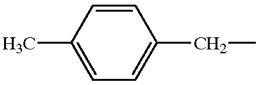 | 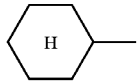 | Br⁻ |
| III-8 | 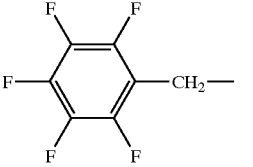 | 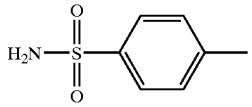 | TsO⁻ |
| III-9 | 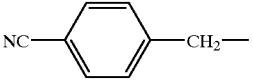 | 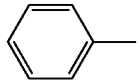 | Br⁻ |
| III-10 | 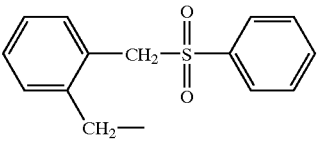 | 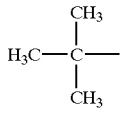 | PF$_6^-$ |
| III-11 | 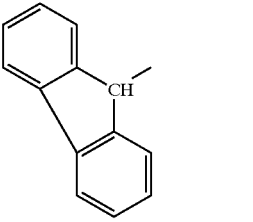 | 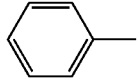 | Br⁻ |
| III-12 | 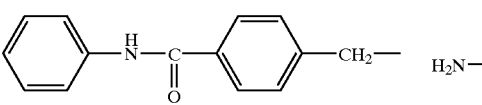 | 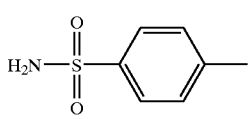 | TsO⁻ |
| III-13 | 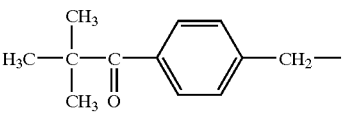 | 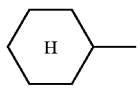 | TsO⁻ |

-continued
| | R² | R³ | X⁻ |
|---|---|---|---|
| III-14 | 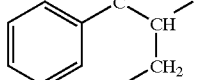 |  | TsO⁻ |
| III-15 | 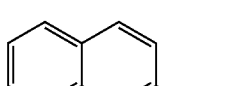 | 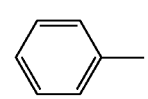 | TsO⁻ |
| III-16 | MeOCO—⟨C₆H₄⟩—CH₂— |  | TsO⁻ |
| III-17 | 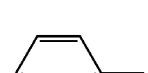 | 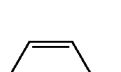 | TsO⁻ |
| Compound No. | R² | R³ | X⁻ |
|---|---|---|---|
| IV-1 | H₃C—CH₂—CH₂—CH₂—CH₂—CH₂— | phenyl | I⁻ |
| IV-2 | benzyl | 2-hydroxy-5-methylbenzyl | PF₆⁻ |
| IV-3 | 4-methylbenzyl | phenyl | Br⁻ |
| IV-4 | 4-methylbenzyl | cyclohexyl | Br⁻ |
| IV-5 | 2,3,5,6-tetrafluoro-4-(trifluoromethyl)benzyl | 2-hydroxy-5-methylbenzyl | Br⁻ |
| IV-6 | 1-phenylethyl | phenyl | PF₆⁻ |
| IV-7 | 4-methylbenzyl | cyclohexyl | Br⁻ |

-continued
| | | | |
|---|---|---|---|
| IV-8 | 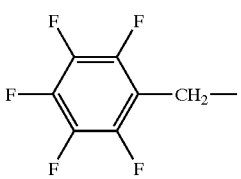 | 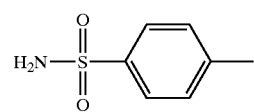 | TsO⁻ |
| IV-9 | 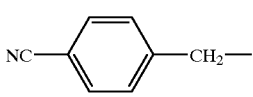 | 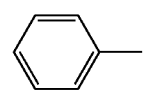 | Br⁻ |
| IV-10 | 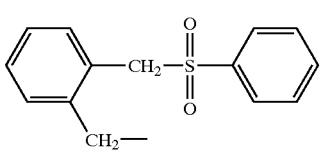 | 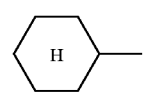 | PF$_6^-$ |
| IV-11 | 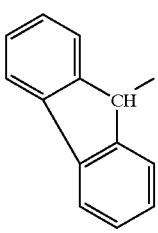 | 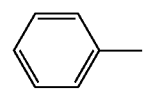 | Br⁻ |
| IV-12 | 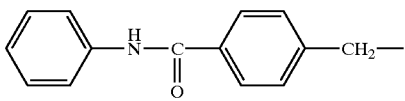 | 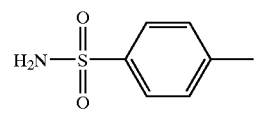 | TsO⁻ |
| IV-13 | 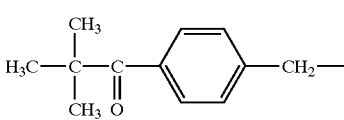 | 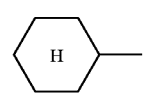 | TsO⁻ |
| IV-14 | 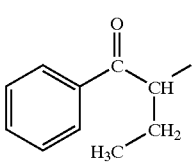 | 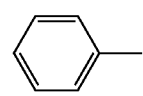 | TsO⁻ |
| IV-15 | 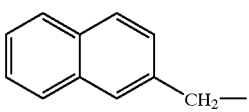 | 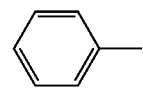 | TsO⁻ |
| IV-16 | 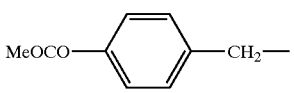 | 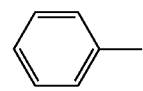 | TsO⁻ |
| IV-17 | 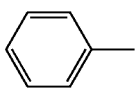 | 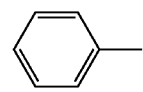 | TsO⁻ |

Also, the following various compound represented by the compounds No. V.1 to V.22 are preferably used as the compounds represented by the general formula (1) which can produce the effect of the invention.
V-1
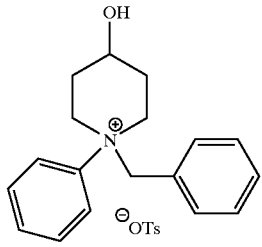
V-2
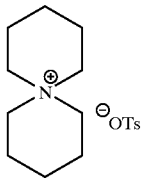
V-3
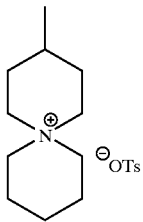
V-4
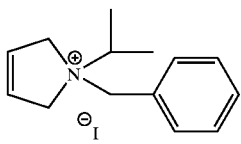
V-5
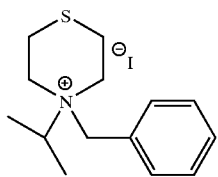
V-6
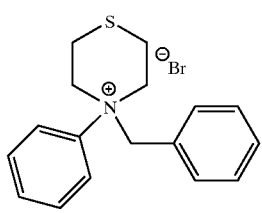
V-7
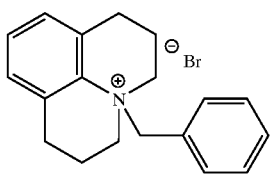
V-8
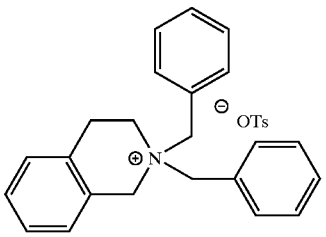
V-9
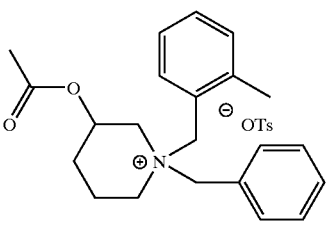
V-10
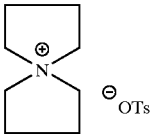
V-11
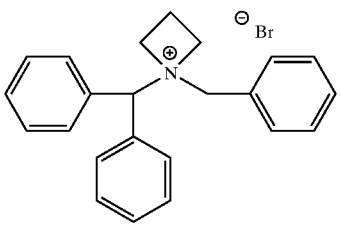
V-12
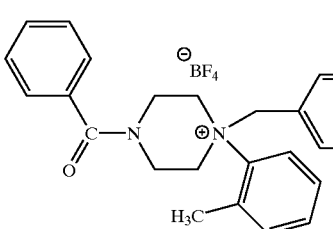
V-13
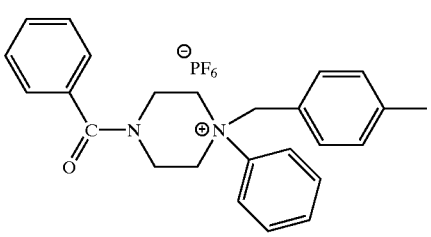
V-14
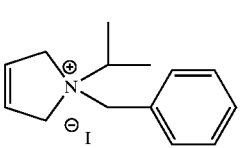

V-15 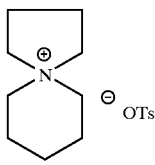

V-16 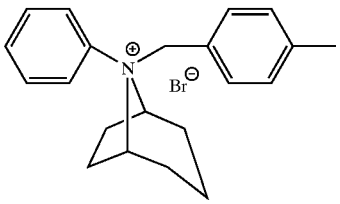

V-17 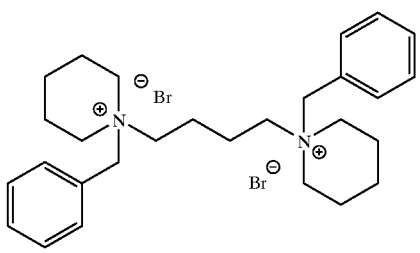

V-18 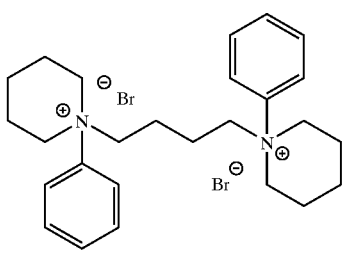

V-19 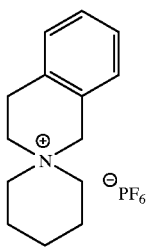

V-20 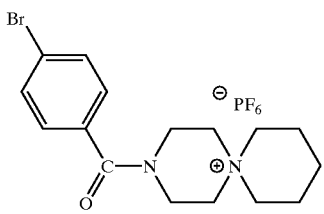

V-21 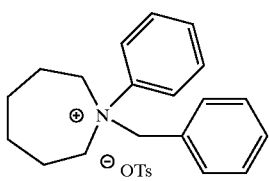

V-22 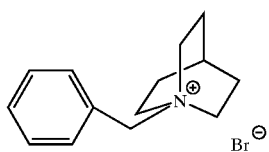

Among the compounds represented by the general formula (1), compounds having a structure in which the ring containing $N^1$ atom is a six-membered alicyclic ring (piperidine ring) and which has an aromatic ring connected directly to the $N^1$ atom and an aromatic ring bonded to the $N^1$ atom via $CH_2$, namely the ammonium compounds represented by the following general formula (1-N) are novel compounds and may be preferably used for the image forming material of the invention.

General Formula (1-N)

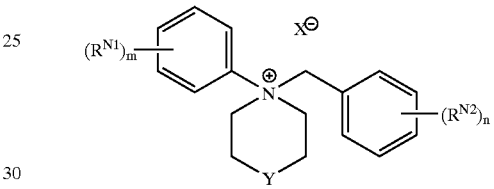

In the general formula, $R^{N1}$ and $R^{N2}$ independently represent a substituent selected from an alkyl group, alkenyl group, alkynyl group, aryl group, amino group, alkoxy group, aryloxy group, acyl group, alkoxycarbonyl group, aryloxycarbonyl group, acyloxy group, acylamino group, alkoxycarbonylamino group, aryloxycarbonylamino group, sulfonylamino group, sulfamoyl group, carbamoyl group, alkylthio group, arylthio group, sulfonyl group, hydroxyl group, mercapto group, halogen atom, cyano group, sulfo group, carboxyl group and nitro group and m and n independently denote an integer from 0 to 5. When plural $R^{N1}$s and $R^{N2}$s are respectively present, plural $R^{N1}$s and $R^{N2}$s may be respectively the same or different and may independently bond to each other to form a ring. $R^{N1}$ and $R^{N2}$ may be cyclic compounds, straight-chain compounds or compounds having a branched chain. These compounds may have a substituent selected from the same group.

Y represents —$CH_2$—, —O— or —S—.

In the general formula (1-N), compounds having this structure containing the piperidine ring and two aromatic rings are novel compounds. There is no particular limitation to the counter anion ($X^-$) and those having the same meaning as in the general formula (1) may be applied. That is, $X^-$ represents an anion corresponding to a conjugate base of an organic or inorganic acid. $X^-$ may be anions corresponding to an organic acid conjugate base, such as $R^{a1}$—$SO_3^-$, $R^{a1}$—$SO_2^-$, $R^{a1}$—$CO_2^-$, $R^{a1}$—O—$PO_2^-$, $(R^{a1}$—$O)_2PO_2^-$, $R^{a1}(R^{a1}$—$O)PO_2^-$, $R^{a1}$-$EW^1$-$Z^-$-$EW^2$-$R^{a1}$, $(R^{a1})_4B^-$ and $Ar^xO^-$ or anions corresponding to an inorganic acid conjugate base, such as $F^-$, $Cl^-$, $Br^-$, $I^-$, $PF_6^-$, $BF_4^-$, $SbF_6^-$, $ClO_4^-$, $SCN^-$, $CN^-$, $SiF_6^-$ and $FSO_3^-$, wherein $R^{a1}$ is an organic substituent and represents an alkyl group, an alkenyl group, an alkynyl group, an aryl group, an aralkyl group or groups obtained by substituting these groups. When plural $R^{a1}$s are present in the molecule, they may be selected independently or may bond to each other to form a ring, $EW^1$ and $EW^2$ independently represent an electron attractive group and specific examples of these groups may include —SO—, —CO—, —$SO_2$—, —CN—, —$NO_2$ and —$CF_3$. Z represents —$CR^{z1}$— or —N— ($R^{z1}$ represents a hydrogen atom or a substituent). $Ar^x$ represents a substituted or unsubstituted aryl group.

Specific examples of the novel ammonium compound having such a structure include the compounds (I-2) to (I-4), (I-6) to (I-11), (I-39), (I-41), (I-45), (I-51), (I-53), (I-59), (IV-3), (IV-9), (IV-12), (IV-15), (IV-16) and (V-6) among the compounds exemplified above.

Typical synthetic examples of the compounds represented by the general formula (1-N) will be hereinafter explained.

SYNTEHTIC EXAMPLE 1

Synthesis of 1-(4-methylphenyl)piperidine

A reaction container was charged with 1,5-dibromopentane (43 g, 186.6 mmol), sodium carbonate (30 g, 280 mmol) and 100 ml of methanol which were weighed and the mixture was stirred at ambient temperature. Then, p-toluidine (10 g, 93.3 mmol) was dissolved in methanol (50 ml) and the solution was added dropwise to the reaction solution. The reaction solution was heated to 55° C. and stirred for 5 hours. The reaction solution was filtered and the resulting filtrate was concentrated under a reduced pressure. The resulting oily mixture was dissolved in ethyl acetate, which was washed with aqueous saturated sodium bicarbonate by using a separating funnel and extracted with 3% hydrochloric acid. Sodium bicarbonate was added to the water phase with stirring the water phase to neutralize it and then the water phase was extracted with ethyl acetate three times. The resulting ethyl acetate solutions were combined and the combined solution was dried using magnesium sulfate and filtered and the filtrate was concentrated under a reduced pressure and distilled under a reduced pressure to obtain 1-(4-methylphenyl)piperidine (8.2 g, yield: 50.3%).

[Boiling point (BP): 110 to 112° C. (2.2 mmHg) 1H-NMR ($CDCl_3$, 300 MHz): 7.07 (d, 2H), 6.86 (d, 2H), 3.09 (t, 4H), 2.27 (s, 3H), 1.73 (qui, 4H), 1.5–1.65 (multi, 2H)]

SYNTHETIC EXAMPLE 2

Synthesis of 4-methylbenzyl(4-methylphenyl) piperidinium bromide

A reaction container was charged with 1-(4-methylphenyl)piperidine (4.0 g, 22.8 mmol) and 10 ml of acetone and the mixture was stirred at ambient temperature. Then, α-bromo-p-xylene (5 g, 27.4 mmol) was added to the reaction solution. The reaction solution was stirred for 3 hours and 20 ml of ethyl acetate was added to the solution. The reaction mixture was further stirred for 30 minutes and subjected to suction filtration to collect a white powder. The resulting powder was dried to obtain 4-methylbenzyl(4-methylphenyl)piperidiniumbromide (6.8 g, yield: 83%).

[Melting point (mp.): 135 to 137° C. 1H-NMR($CDCl_3$, 300 MHz): 7.33 (d, 2H) 7.25 (d, 2H) 6.95 (d, 2H), 6.83 (d, 2H), 5.28 (s, 2H), 4.89 (t, 2H), 4.31 (d, 2H), 2.43 (s, 3H), 1.8–2.1 (multi, 3H), 1.5–1.7 (multi, 3H)]

SYNTHETIC EXAMPLE 3

Synthesis of 4-methylphenylbenzylpiperidinium hexafluorophosphate

An aqueous solution prepared by dissolving 4-methylphenylbenzylpiperidinium bromide (13.85 g, 0.04 mmol) in 20 ml of deionized water was mixed with an aqueous solution prepared by dissolving potassium hexafluorophosphate ($KPF_6$, 8.83 g, 0.048 mmol) in 30 ml of deionized water and the produced white solid was collected by filtration. The resulting white solid was washed with 300 ml of deionized water, subjected to filtration and dried to obtain 4-methylphenylbenzylpiperidinium hexafluorophosphate (15.6 g, yield: 95%).

[mp. 203–204° C.; 1H-NMR($CDCl_3$, 300 MHz): 7.4–7.6 (multi, 5H), 6.98 (d, 2H), 6.83 (d, 2H), 5.40 (d, 2H), 4.90 (t, 2H), 4.42 (d, 2H), 2.25 (s, 3H), 1.8–2.1 (multi, 3H), 1.5–1.7 (multi, 3H)]

SYNTHETIC EXAMPLE 4

Synthesis of 4-methylphenylbenzylpiperidinium tosylate

An aqueous solution prepared by dissolving 4-methylphenylbenzylpiperidinium bromide (13.85 g, 0.04 mmol) and sodium p-toluenesulfonate (9.32 g, 0.048 mmol) in 50 ml of deionized water was extracted with 50 ml of chloroform twice by using a separating funnel. The resulting chloroform phases were combined and the combined solution was washed with 50 ml of deionized water, followed by filtration and drying to obtain 4-methylphenylbenzylpiperidinium tosylate (16.1 g, yield: 92%).

[mp. 176–177° C.; 1H-NMR($CDCl_3$, 300 MHz): 7.91 (d, 2H), 7.45 (t-3H), 7.37 (multi, 2H), 7.16 (d, 2H), 6.89 (d, 2H), 6.64 (d, 2H), 5.06 (s, 2H), 4.55 (t, 2H), 4.36 (d, 2H), 2.36 (s, 3H), 2.23 (s, 3H), 1.8–2.0 (multi, 3H), 1.5–1.7 (multi, 3H)]

The compounds represented by the general formula (1) to be used in the image forming material of the invention may be used either singly or in combinations of two or more. The content of the compound is preferably 50% or less from the viewpoint of film forming ability, preferably in a range from 0.1% to 30% with the view of obtaining significantly good image forming ability and most preferably in a range from 0.5% to 15% as the amount enabling the compatibility between printing qualities such as printing durability and image forming characteristics at a higher level.

Water-Insoluble and Alkali-Soluble Resin (A) The water-insoluble and alkali-soluble resin (hereinafter, referred to as an alkali soluble resin as the case may be) to be used for the positive image forming layer according to the invention include homopolymers and copolymers containing an acidic group on the primary chain and/or the side chain in a polymer and mixtures of these polymers.

Among these polymers, those containing the acidic groups given in the following (1) to (6) on the primary chain and/or the side chain thereof are preferable in view of solubility in an alkaline developing solution and the manifestation of dissolution inhibitive ability.

(1) Phenol group (—Ar—OH)
(2) Sulfonamide group (—$SO_2$NH—R)
(3) Substituted sulfonamide type acidic group (hereinafter referred to as "active imide group") [—$SO_2$NHCOR, —$SO_2$NH$SO_2$R and —CONH$SO_2$R]
(4) Carboxylic acid (—$CO_2$H)
(5) Sulfonic acid group (—$SO_3$H)
(6) Phosphoric acid group (—$OPO_3H_2$)

In the (1) to (6), Ar represents a divalent aryl connecting group which may have a substituent and R represents a hydrocarbon group which may have a substituent.

Among the alkali-soluble resins having an acidic group selected from the (1) to (6), alkali-soluble resins having (1) a phenol group, (2) a sulfonamide group and/or (3) an active imide group are preferable and, particularly, alkali-soluble resins having (1) a phenol group or (2) a sulfonamide group are most preferable with the view of securing solubility in an alkaline developer, development latitudes and film strength sufficiently.

As the alkali-soluble resins having an acidic group selected from the (1) to (6), the following compounds may be exemplified.

(1) Examples of the alkali-soluble resin having a phenol group may include novolac resins such as condensed polymers of phenol and formaldehyde, condensed polymers of m-cresol and formaldehyde, condensed polymers of p-cresol and formaldehyde, condensed polymers of m-/p-mixed cresol and formaldehyde and phenol, cresol (may be any of m-, p- or a mixture of m-/p-) and formaldehyde and condensed polymers of pyrogallol and acetone. Further, copolymers prepared by copolymerizing compounds having a phenol group on the side chain may be exemplified.

Examples of the compound having a phenol group may include acrylamides, methacrylamides, acrylates, methacrylates having a phenol group or hydroxystyrene.

(2) Examples of the alkali-soluble resin having a sulfonamide group may include polymers having as its major constitutional component a minimum structural unit derived from a compound having a sulfonamide group. As compounds such as those described above, compounds having one or more sulfonamide groups in which at least one hydrogen atom is bonded to a nitrogen atom and one or more polymerizable unsaturated groups in a molecule are given as examples. Among these compounds, low molecular compounds having an acryloyl group, aryl group or vinyloxy group and substituted or mono-substituted aminosulfonyl group or substituted sulfonylimino group in a molecule are preferable. The compounds represented by the following formulae (i) to (v) are exemplified as such a low molecular compound.

General Formula (i)
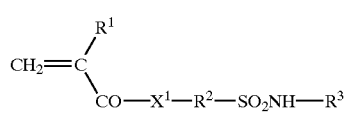

General Formula (ii)
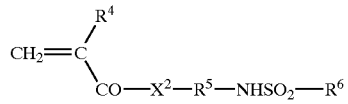

General Formula (iii)
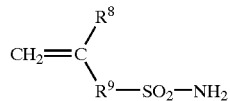

General Formula (iv)
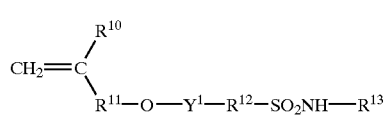

General Formula (v)
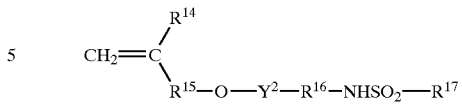

wherein $X^1$ and $X^2$ independently represent —O— or —$NR^7$, $R^1$ and $R^4$ independently represent a hydrogen atom or —$CH_3$; $R^2$, $R^5$, $R^9$, $R^{12}$ and $R^{16}$ independently represent an alkylene group, a cycloalkylene group, an arylene group or an aralkylene group having 1 to 12 carbon atoms and may have a substituent; $R^3$, $R^7$ and $R^{13}$ independently represent a hydrogen atom or an alkyl group, a cycloalkyl group, an aryl group or an aralkyl group having 1 to 12 carbon atoms and may have a substituent; $R^6$ and $R^{17}$ independently represent an alkyl group, a cycloalkyl group, an aryl group or an aralkyl group having 1 to 12 carbon atoms and may have a substituent; $R^8$, $R^{10}$ and $R^{14}$ independently represent a hydrogen atom or —$CH_3$; $R^{11}$ and $R^{15}$ independently represent a single bond, an alkylene group, a cycloalkylene group, an arylene group or an aralkylene group having 1 to 12 carbon atoms and may have a substituent; and $Y^1$ and $y^2$ independently represent a single bond or CO.

Among the compounds represented by the formulae (i) to (v), particularly m-aminosulfonylphenyl methacrylate, N-(p-aminosulfonylphenyl)methacrylamide, N-(p-aminosulfonylphenyl) acrylamide and the like may be preferably used for the positive planographic printing plate of the invention.

(3) Examples of the alkali-soluble resin having an active imide group may include polymers having as its major constitutional component a minimum structural unit derived from a compound having an active imide group are given as examples. Examples of compounds such as those described above may include compounds containing one or more active imide groups represented by the following structural general formula and one or more polymerizable unsaturated group in a molecule.

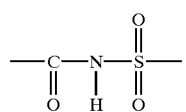

Specifically, N-(p-toluenesulfonyl)methacrylamide, N-(p-toluenesulfonyl)acrylamide and the like may be preferably used.

(4) Examples of the alkali-soluble resin having a carboxylic acid group may include polymers having as its major constitutional component a minimum structural unit derived from a compound having one or more carboxylic acid groups and one or more polymerizable unsaturated groups in a molecule.

(5) Examples of the alkali-soluble resin having a sulfonic acid group may include polymers having as its major constitutional component a minimum structural unit derived from a compound having one or more sulfonic acid groups and one or more polymerizable unsaturated groups in a molecule.

(6) Examples of the alkali-soluble resin having a phosphoric acid group may include polymers having as its major constitutional component a minimum structural unit derived from a compound having one or more phosphoric acid groups and one or more polymerizable unsaturated groups in a molecule.

The minimum structural unit having an acidic group selected from the foregoing (1) to (6), which unit constitutes the alkali-soluble resin to be used in the positive image forming layer is not limited to only one type and alkali-soluble resins obtained by copolymerizing two or more minimum structural units having either the same acidic groups or different acidic groups may be used.

The copolymer is those containing the compound which has an acidic group selected from the above (1) to (6) and is to be polymerized in an amount of preferably 10 mol % or more and more preferably 20 mol % or more in the copolymer. When the amount is less than 10 mol %, there is a tendency that the developing latitude is insufficiently improved.

In the invention, when a copolymer is used as an alkali-soluble resin, a compound which does not contain the acidic group of the above (1) to (6) may also be used. Examples of the compound which does not contain the acidic group of the above (1) to (6) may include the compounds described in the following (m1) to (m12). These compounds, however, are not intended to be limiting of the invention.

(m1) Acrylates and methacrylates having an aliphatic hydroxyl group such as 2-hydroxyethyl acrylate or 2-hydroxyethyl methacrylate.
(m2) Alkyl acrylates such as methyl acrylate, ethyl acrylate, propyl acrylate, butyl acrylate, amyl acrylate, hexyl acrylate, octyl acrylate, benzyl acrylate, 2-chloroethyl acrylate and glycidyl acrylate.
(m3) Alkyl methacrylates such as methyl methacrylate, ethyl methacrylate, propyl methacrylate, butyl methacrylate, amyl methacrylate, hexyl methacrylate, cyclohexyl methacrylate, benzyl methacrylate, 2-chloroethyl methacrylate and glycidyl methacrylate.
(m4) acrylamides or methacrylamides such as acrylamide, methacrylamide, N-methylolacrylamide, N-ethylacrylamide, N-hexylmethacrylamide, N-cyclohexylacrylamide, N-hydroxyethylacrylamide, N-phenylacrylamide, N-nitrophenylacrylamide and N-ethyl-N-phenylacrylamide.
(m5) Vinyl ethers such as ethyl vinyl ether, 2-chloroethyl vinyl ether, hydroxyethyl vinyl ether, propyl vinyl ether, butyl vinyl ether, octyl vinyl ether and phenyl vinyl ether.
(m6) Vinyl esters such as vinyl acetate, vinyl chloroacetate, vinyl butyrate and vinyl benzoate.
(m7) Styrenes such as styrene, α-methylstyrene, methylstyrene and chloromethylstyrene.
(m8) Vinyl ketones such as methyl vinyl ketone, ethyl vinyl ketone, propyl vinyl ketone and phenyl vinyl ketone.
(m9) Olefins such as ethylene, propylene, isobutylene, butadiene and isoprene.
(m10) N-vinylpyrrolidone, acrylonitrile, methacrylonitrile and the like.
(m11) Unsaturated imides such as maleimide, N-acryloylacrylamide, N-acetylmethacrylamide, N-propionylmethacrylamide and N-(p-chlorobenzoyl) methacrylamide.
(m12) Unsaturated carboxylic acids such as acrylic acid, methacrylic acid, maleic acid anhydride and itaconic acid.

The alkali-soluble resin having a phenolic hydroxyl group is preferable in view of excellent image-forming ability in exposure using an infrared laser or the like. Specifically, novolac resins such as phenol-formaldehyde resins, m-cresol-formaldehyde resins, p-cresol-formaldehyde resins, m-/p-mixed cresol-formaldehyde resins and phenol/cresol (may be any of m-, p- or a mixture of m-/p-)-formaldehyde resins and pyrogallol-acetone resins are more preferable.

Also, given as further examples of the alkali-soluble resin having a phenolic hydroxyl group are condensates of phenols containing an alkyl group having 3 to 8 carbon atoms as a substituent and formaldehyde, such as t-butylphenol-formaldehyde resins and octylphenol-formaldehyde resins as described in the specification of U.S. Pat. No. 4,123,279.

The alkali-soluble resin has a weight average molecular weight of 500 or more and more preferably 1,000 to 700,000 in view of image forming ability. Also, its number average molecular weight is preferably 500 or more and more preferably 750 to 650,000. The degree of dispersion (weight average molecular weight/number average molecular weight) of the alkali-soluble resin is preferably 1.1 to 10.

Also, these alkali-soluble resins may be used either singly or in combinations of two or more. When the combinations are used, condensates of phenols having an alkyl group having 3 to 8 carbon atoms as a substituent and formaldehyde, such as condensates of t-butylphenol and formaldehyde and condensates of octylphenol and formaldehyde as described in the specification of U.S. Pat. No. 4,123,279, and the alkali-soluble resin having a phenol structure having an electron attractive group on an aromatic ring as described in JP-A No. 2000-241972 submitted previously by the inventors of the invention may be used together.

The total content of the alkali-soluble resin in the invention is preferably 30 to 98% by weight and more preferably 40 to 95% by weight based on the total solid of the image forming layer. When the content is less than 30% by weight, the durability tends to be impaired whereas when the content exceeds 98% by weight, the sensitivity and the image formability tend to be reduced.

Light-Heat Converting Agent

As the light-heat converting agent used in the invention, any material may be used without any limitation to the absorption wavelength range as far as it is a material which absorbs the light-energy radiation used for recording to generate heat. However, infrared-absorbable dyes and pigments having an absorption maximum in a wavelength range from 760 nm to 1200 nm are preferable from the viewpoint of adaptability to an easily available high-output laser.

As the dye, commercially available dyes and, for example known dyes described in literature such as "Dye Handbook" (edited by Organic Synthetic Chemical Association, published in 1970) may be utilized. Specific examples of these dyes may include azo dyes, metal complex azo dyes, pyrazolone azo dyes, naphthoquinone dyes, anthraquinone dyes, phthalocyanine dyes, carbonium dyes, quinoneimide dyes, methine dyes, cyanine dyes, squalilium dyes, pyrylium salts, metal thiolate complexes, oxonol dyes, diimmonium dyes, aminium dyes and croconium dyes.

Preferable examples of the dye may include cyanine dyes described in JP-A Nos. 58-125246, 59-84356, 59-202829, 60-78787 and the like and methine dyes described in JP-A Nos. 58-173696, 58-181690, 58-194595 and the like, naphthoquinone dyes described in JP-A Nos. 58-112793, 58-224793, 59-48187, 59-73996, 60-52940, 60-63744 and the like, squalilium dyes described in JP-A No. 58-112792 and the like and cyanine dyes described in U.K. patent No. 434,875.

Near-infrared absorbing sensitizer described in U.S. Pat. No. 5,156,938 are also preferably used. Substituted arylbenzo(thio)pyrylium salts described in U.S. Pat. No. 3,881,924, trimethinethiapyrylium salts described in JP-A No. 57-142645 (U.S. Pat. No. 4,327,169), pyrylium compounds described in JP-A Nos. 58-181051, 58-220143, 59-41363, 59-84248, 59-84249, 59-146063 and 59-146061, cyanine dyes described in JP-A No. 59-216146, pentamethinethiopyrylium salts and the like described in U.S. Pat. No. 4,283,475 and pyrylium compounds disclosed in Japanese Patent Application Publication (JP-B) Nos. 5-13514 and 5-19702 are also preferably used.

Also, other preferable examples of the dye may include near-infrared absorbing dyes represented by the formulae (I) or (II) described in the specification of U.S. Pat. No. 4,756,993.

As examples of particularly preferable dyes among these dyes, cyanine dyes, phthalocyanine dyes, oxonol dyes, squalilium dyes, pyrylium salts, thiopyrylium dyes and nickel thiolate complexes are given. Moreover, dyes represented by the following formulae (a) to (e) are preferable because these dyes have superior light-heat conversion efficiency. In particular, cyanine dyes represented by the following general formula (a) are most preferable because these dyes impart high polymerization activity when used in the polymerizable composition according to the invention and have high stability and profitability.

General Formula (a)

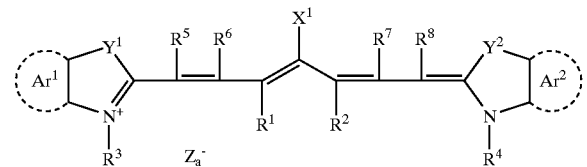

In the general formula (a), $X^1$ represents a hydrogen atom, a halogen atom, —$NPh_2$, $X^2$-$L^1$ or a group shown below. Here, $X^2$ represents an oxygen atom or a sulfur atom, $L^1$ represents a hydrocarbon group having 1 to 12 carbon atoms, an aromatic ring having a heteroatom or a hydrocarbon group containing a heteroatom and having 1 to 12 carbon atoms. Here, the heteroatom represents N, S, O, a halogen atom or Se.

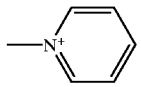

$R^1$ and $R^2$ independently represent a hydrocarbon group having 1 to 12 carbon atoms. $R^1$ and $R^2$ are independently preferably a hydrocarbon group having 2 or more carbon atoms in view of the preservation stability of a light-sensitive layer coating solution and, moreover, $R^1$ and $R^2$ particularly preferably bond to each other to form a five-membered or six-membered ring.

$Ar^1$ and $Ar^2$, which may be the same or different, independently represent an aromatic hydrocarbon group which may have a substituent. Preferable examples of the aromatic hydrocarbon group include a benzene ring or naphthalene ring. Also, preferable examples of the substituent include hydrocarbon groups having 12 or less carbon atoms, halogen atoms and alkoxy groups having 12 or less carbon atoms. $Y^1$ and $Y^2$, which may be the same or different, independently represent a sulfur atom or a dialkylmethylene group having 12 or less carbon atoms. $R^3$ and $R^4$, which may be the same or different, independently represent a hydrocarbon group which may have a substituent and has 20 or less carbon atoms. Preferable examples of the substituent include alkoxy groups having 12 or less carbon atoms, carboxyl groups and sulfo groups. $R^5$, $R^6$, $R^7$ and $R^8$, which may be the same or different, independently represent a hydrogen atom or a hydrocarbon group having 12 or less carbon atoms. A hydrogen atom is preferable from the viewpoint of the availability of raw materials. Also, $Za^-$ represents a counter anion. In the case where any one of $R^1$ to $R^8$ is substituted with a sulfo group, $Za^+$ is not required. $Za^-$ is preferably halogen ions, perchloric acid ions, tetrafluoroborate ions, hexafluorophosphate ions and sulfonic acid ions and particularly preferably perchloric acid ions, hexafluorophosphate ions and arylsulfonic acid ions in view of the preservation stability of a light-sensitive layer coating solution.

In the invention, specific examples of the cyanine dyes which are represented by the general formula (a) and preferably used may include those described in the specification of Japanese Patent Application No. 11-310623, paragraphs No. [0017] to No. [0019], the specification of Japanese Patent Application No. 2000-224031, paragraphs No. [0012] to No. [0038] and the specification of Japanese Patent Application No. 2000-211147, paragraphs No. [0012] to No. [0023], besides dyes exemplified below.

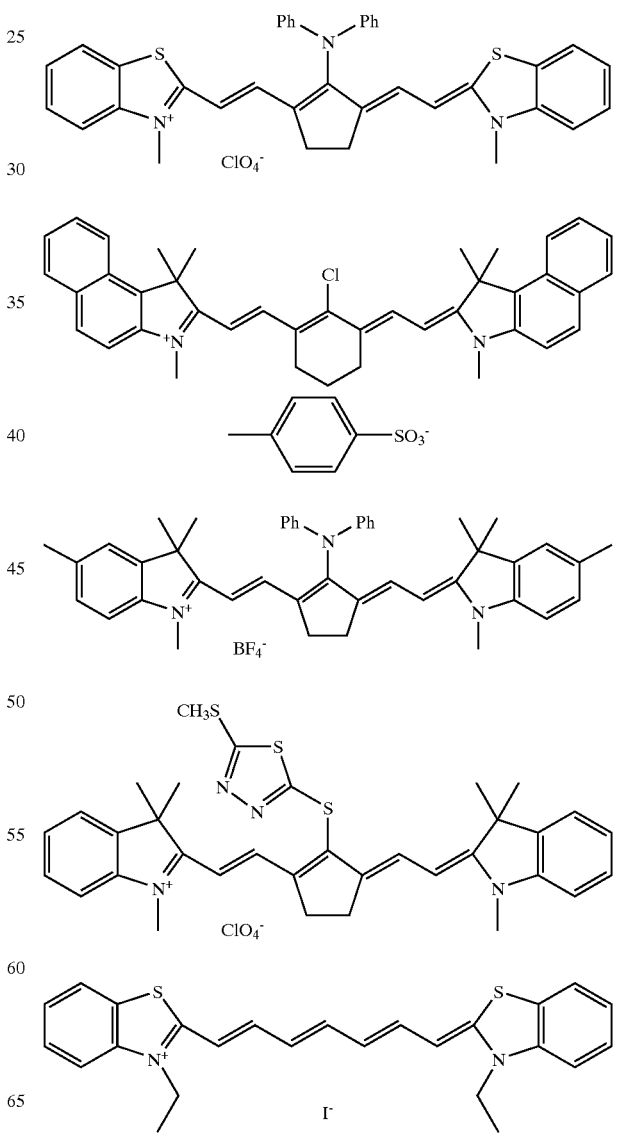

-continued

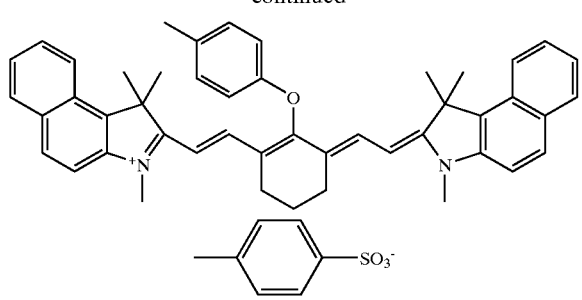

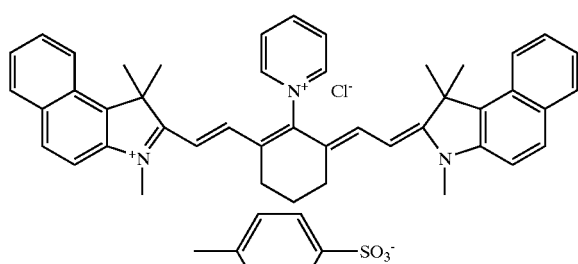

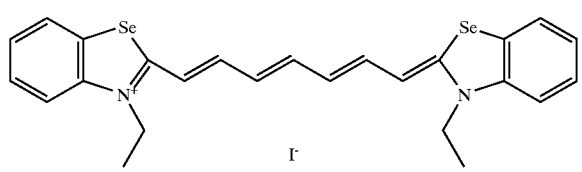

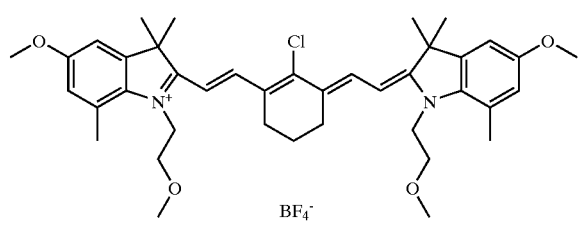

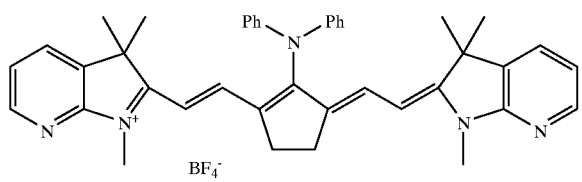

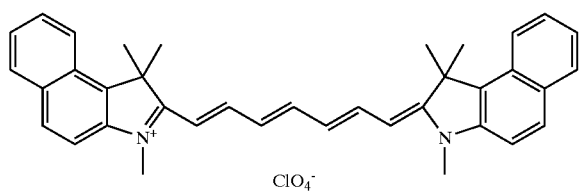

-continued

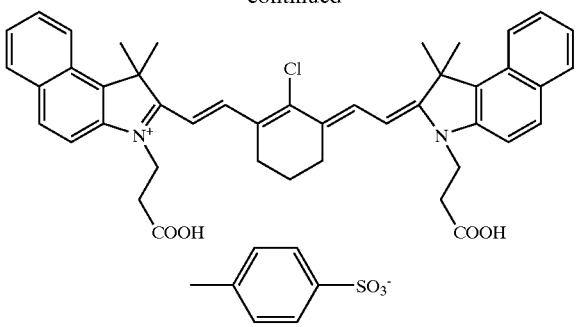

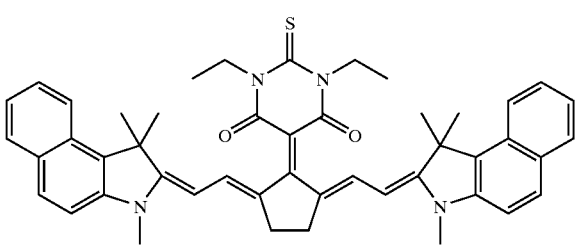

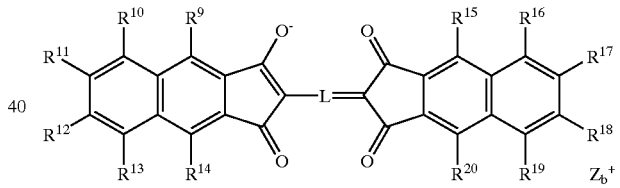

General Formula (b)

In the general formula (b), L represents a methine chain having 7 or more conjugate carbon atoms. The methine chain may have a substituent and the substituents may bond to each other to form a ring. $Z_b^+$ represents a counter cation. Preferable examples of the counter cation include ammonium, iodonium, sulfonium, phosphonium, pyridinium and alkali metal cations ($Ni^+$, $K^+$ and $Li^+$). $R^9$ to $R^{14}$ and $R^{15}$ to $R^{20}$ independently represent a hydrogen atom or a substituent selected from a halogen atom, a cyano group, an alkyl group, an aryl group, an alkenyl group, an alkynyl group, a carbonyl group, a thio group, a sulfonyl group, a sulfinyl group, an oxy group and an amino group or a substituent of a combination of two or three of these groups and may bond to each other to form a ring. Here, compounds in which L represents a methine chain having 7 conjugate carbon atoms and compounds in which all of $R^9$ to $R^{14}$ and $R^{15}$ to $R^{20}$ represent hydrogen atoms in the general formula (b) are preferable from the viewpoint of availability and effects.

In the invention, specific examples of the dyes represented by the general formula (b) and preferably used may include the following compounds.

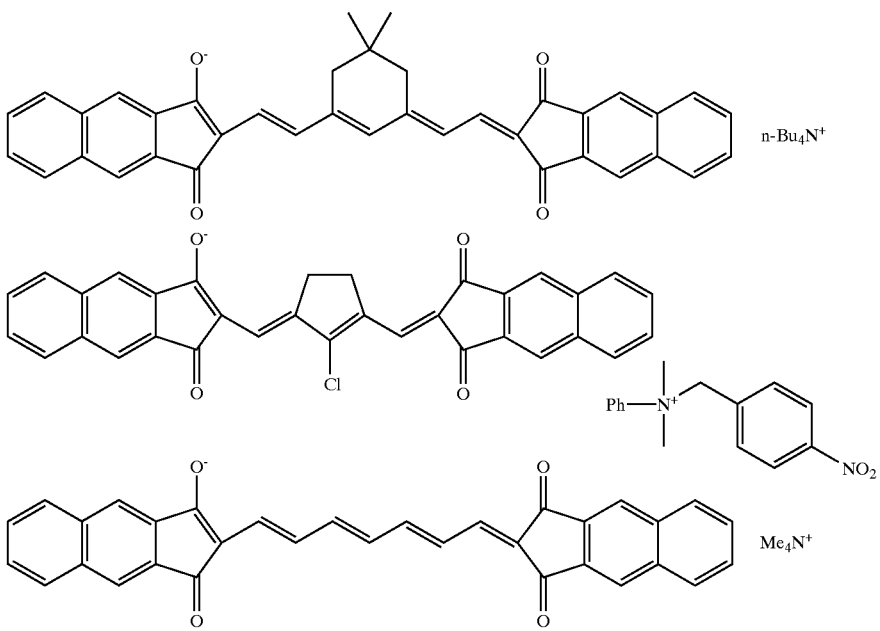

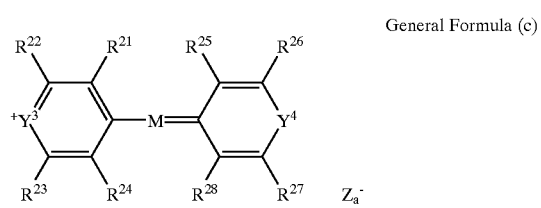

General Formula (c)

In the general formula (c), $Y^3$ and $Y^4$ independently represent an oxygen atom, a sulfur atom, a selenium atom or a tellurium atom. M represents a methine chain having 5 or more conjugate carbon atoms. $R^{21}$ to $R^{24}$ and $R^{25}$ to $R^{28}$, which may be the same or different, independently represent a hydrogen atom, a halogen atom, a cyano group, an alkyl group, an aryl group, an alkenyl group, an alkynyl group, a carbonyl group, a thio group, a sulfonyl group, a sulfinyl group, an oxy group or an amino group. Also, in the general formula, $Z_a^-$ represents a counter anion and has the same meaning as in the general formula (a).

In the invention, specific examples of the dyes represented by the general formula (c) and preferably used may include the following compounds.

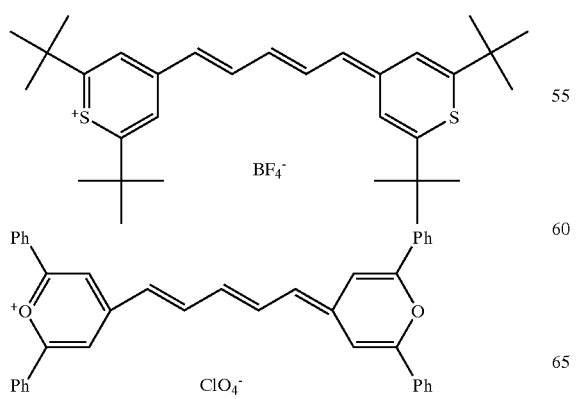

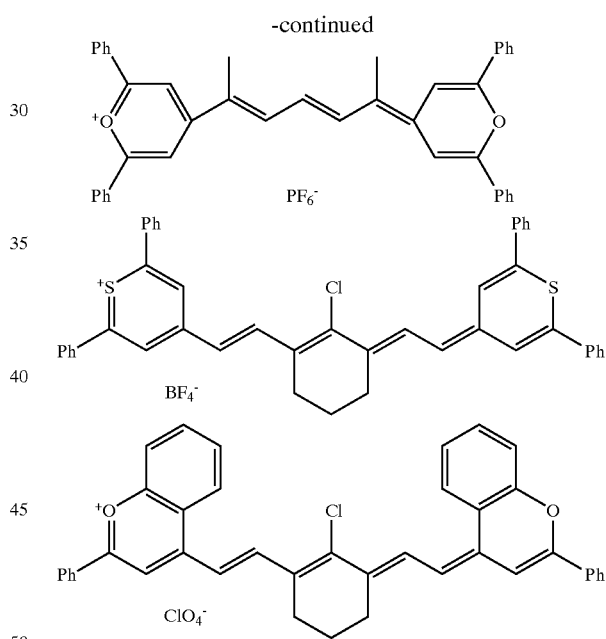

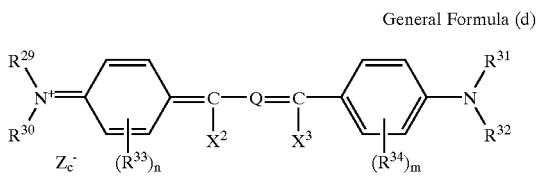

General Formula (d)

In the above general formula (d), $R^{29}$ to $R^{31}$ independently represent a hydrogen atom, an alkyl group or an aryl group. $R^{33}$ and $R^{34}$ independently represent an alkyl group, a substituted oxy group or a halogen atom. n and m independently denote an integer from 0 to 4. $R^{29}$ and $R^{30}$ or $R^{31}$ and $R^{32}$ may bond to each other to form a ring, also, $R^{29}$ and/or $R^{30}$ and $R^{33}$, and $R^{31}$ and/or $R^{32}$ and $R^{34}$ may bond to each other to form a ring. When plural $R^{33}$s and $R^{34}$s are respectively present, $R^{33}$s among them and $R^{34}$s among them may bond to each other to form a ring. $X^2$ and $X^3$ independently represent a hydrogen atom, an alkyl group or an aryl group and at least one of $X^2$ and $X^3$ represents a hydrogen atom or an alkyl group. Q represents a trimethine group or a pentamethine group which may have a substituent and may form a ring in combination with a divalent organic group. $Zc^-$ represents a counter anion and has the same meaning as $Za^-$ in the above general formula (a).

In the invention, specific examples of the dyes represented by the general formula (d) and preferably used may include the following compounds.

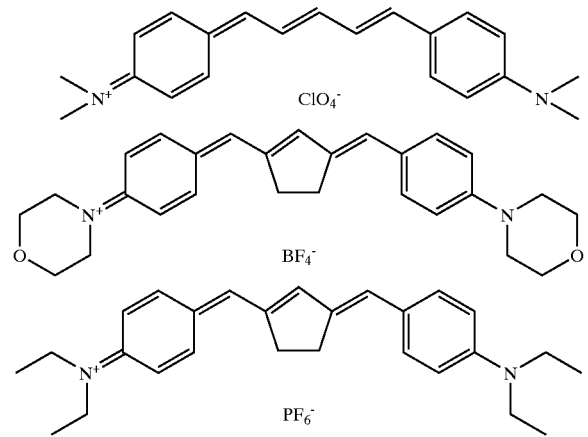

General Formula (e)

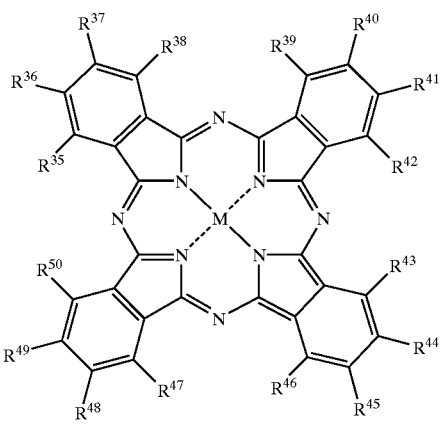

In the above general formula (e), $R^{35}$ to $R^{50}$ independently represent a hydrogen atom, a halogen atom, a cyano group, an alkyl group, an aryl group, an alkenyl group, an alkynyl group, a hydroxyl group, a carbonyl group, a thio group, a sulfonyl group, a sulfinyl group, an oxy group, an amino group or an onium salt structure which may have a substituent. M represents two hydrogen atoms, or a metal salt, a halometal group or an oxymethal group. Examples of the metal atom contained there include IA, IIA, IIIB or IVB group atoms, the first, second or third period transition metals in the periodic table and a lanthanoid element. Among these elements, copper, magnesium, iron, zinc, cobalt, aluminum, titanium and vanadium are preferable.

In the invention, specific examples of the dyes represented by the general formula (e) and preferably used in the invention may include the following compounds.

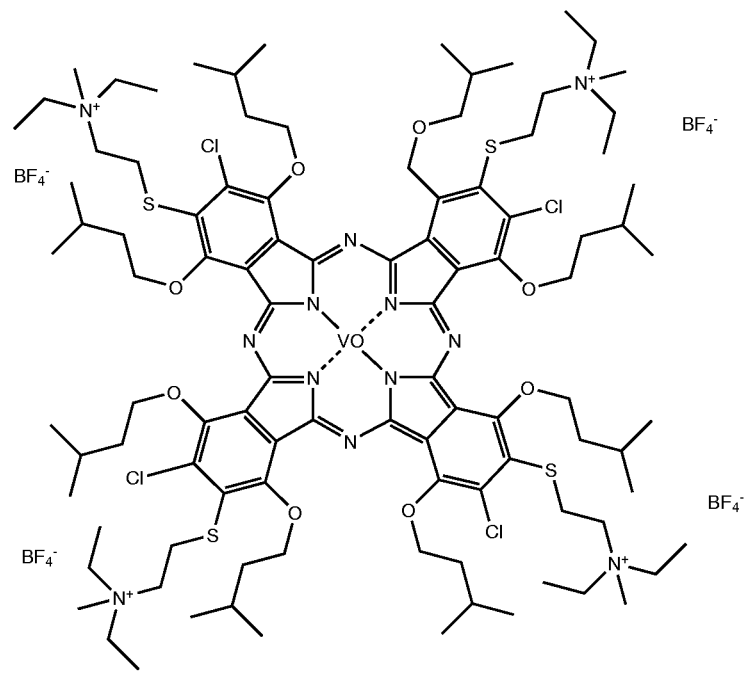

-continued

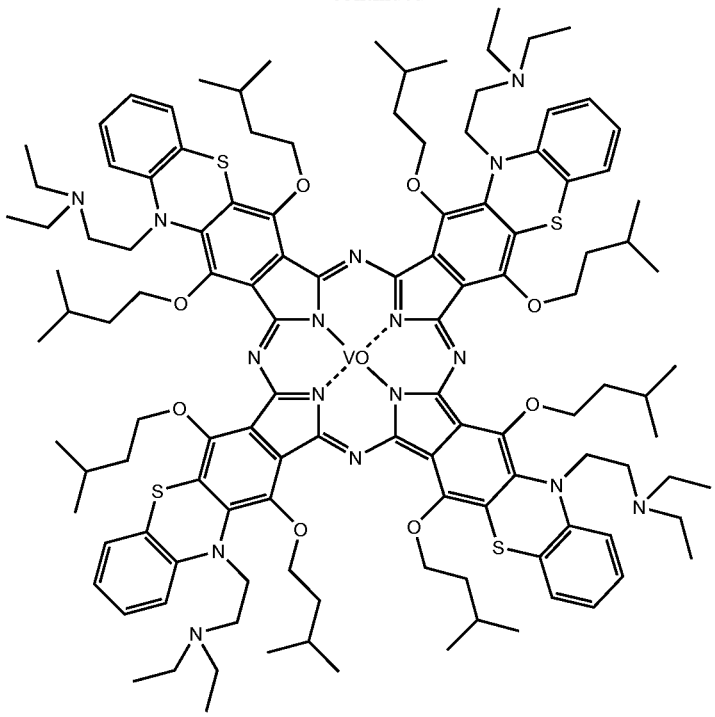

Examples of the pigments to be used as the infrared absorber in the invention include commercially available pigments and pigments described in Color Index (C.I.) Handbook, "LATEST PIGMENT HANDBOOK" (Japan Pigment Technology Association, published in 1977), "LATEST PIGMENT APPLIED TECHNOLOGIES" (CMC Shuppan, published in 1986), "PRINTING INK TECHNOLOGIES" CMC Shuppan, published in 1984).

Examples of the type of pigment, black pigments, yellow pigments, orange pigments, brown pigments, red pigments, violet pigments, blue pigments, green pigments, fluorescent pigments, metal powder pigments and polymer binding dyes. Specifically, insoluble azo pigments, azo lake pigments, condensed azo pigments, chelate azo pigments, phthalocyanine pigments, anthraquinone pigments, perylene and perinone pigments, thioindigo pigments, quinacridone pigments, dioxazine pigments, isoindolinone pigments, quinophthalone pigments, dyeing lake pigments, azine pigments, nitroso pigments, nitro pigment, natural pigments, fluorescent pigments, inorganic pigments and carbon black may be used. Among these pigments, carbon black is desirable.

These pigments may be used either without carrying out surface treatment or after carrying out surface treatment. As surface treating methods, a method in which a resin or wax is applied to pigment grains, a method in which a surfactant is stuck and a method in which a reactive material (e.g., a silane coupling agent, epoxy compound or polyisocyanate) is bound with the surface of a pigment are considered. The surface treating methods are described in "QUALITIES AND APPLICATION OF METAL SOAPS" (Saiwai Shobo), "PLINTING INK TECHNOLOGIES" (CMC Shuppan, published in 1984) and "LATEST PIGMENT APPLIED TECHNOLOGIES" (CMC Shuppan, published in 1986).

The particle diameter of the pigment is preferably in a range from 0.01 $\mu$m to 10 $\mu$m, more preferably in a range from 0.05 $\mu$m to 1 $\mu$m and most preferably in a range from 0.1 $\mu$m to 1 $\mu$m. When the particle diameter is less than 0.01 $\mu$m, this is undesirable in the point of the stability of the dispersion in the coating solution for the image light-sensitive layer. When the particle diameter exceeds 10 $\mu$m, this is undesirable in the point of the uniformity of the image light-sensitive layer.

As a method for dispersing the pigment, known dispersing technologies used for the production of ink or toners may be used. Examples of dispersing machines include a ultrasonic dispersing machine, sand mill, attritor, pearl mill, super mill, ball mill, impeller, disperser, KD mill, colloid mill, dynatron, three-roll mill and pressure kneader. The details of these dispersing machines are described in "LATEST PIGMENT APPLIED TECHNOLOGIES" (CMC Shuppan, published in 1986).

The pigment or dye which is a light-heat converting agent may be added in a proportion of 0.01 to 50% by weight and preferably 0.1 to 30% by weight, and particularly preferably 0.5 to 10% by weight in the case of a dye and 0.1 to 10% by weight in the case of a pigment on the basis of the total solid constituting the image forming layer.

In the case where the pigment or dye is used in the upper layer of a laminated light-sensitive material, the freedom of the amount to be added is higher according to the situation free from a problem concerning developing ability on the interface of the substrate and the pigment or dye may be added in a proportion of 0.01 to 50% by weight, preferably 0.1 to 40% by weight and particularly preferably 0.5 to 30% by weight based on the total solid.

Other Components

When the positive image forming layer according to the invention is formed, various additives may be further added according to the need. For example, materials, such as onium salts, o-quinonediazide compounds, aromatic sulfone compounds and aromatic sulfonates, which are heat-decomposable and substantially lowers the solubility of an aqueous alkali-soluble high molecular compound in a non-decomposed state are preferably used together with the view of improving inhibition of the solubility of an image portion in a developing solution. Examples of the onium salts may include diazonium salts, ammonium salts, phosphonium salts, iodonium salts, sulfonium salts, selenonium salts and arsonium salts.

Preferable examples of the onium salt used in the invention include diazonium salts described in S. I. Schlesinger, Photogr. Sci. Eng., 18, 387 (1974), T. S. Bal et al. Polymer, 21, 423 (1980) and diazonium salts described in the publication of JP-A No. 5-158230, ammonium salts described in each specification of U.S. Pat. Nos. 4,069,055, 4,069,056 and JP-A No. 3-140140, phosphonium salts described in D. C. Necker et al, Macromolecules, 17, 2468 (1984), C. S. Wen at al, Teh, Proc. Conf. Rad. Curing ASIA, p478 Tokyo, October (1988), U.S. Pat. Nos. 4,069,055 and 4,069,056, iodonium salts described in J. V. Crivello et al, Macromolecules, 10(6), 1307 (1977), Chem. & Eng. News, November 28, p31 (1988), E.P. No. 104, 143, U.S. Pat. Nos. 339,049, 410,201, JP-A Nos. 2-150848 and 2-296514, sulfonium salts described in J. V. Crivello et al, Polymer J. 17, 73 (1985), J. V. Crivello et al. J. Org. Chem., 43, 3055 (1978), W. R. Watt et al, J. Polymer Sci., Polymer Chem. Ed., 22, 1789 (1984), J. V. Crivello et al, Polymer Bull., 14, 279 (1985), J. V. Crivello et al, Macromolecules, 14(5), 1141 (1981), J. V. Crivello et al, J. Polymer Sci., Polymer Chem. Ed., 17, 2877 (1979), E.P. Nos. 370, 693, 233,567, 297,443, 297,442, U.S. Pat. Nos. 4,933,377, 3,902,114, 410,201, 339,049, 4,760,013, 4,734,444, and 2,833,827, German Patent Nos. 2,904, 626, 3,604,580 and 3,604,581, selenonium salts described in J. V. Crivello et al, Macromolecules, 10(6), 1307 (1977), J. V. Crivello et al, J. Polymer Sci., and Polymer Chem. Ed., 17, 1047 (1979) and arsonium salts described in C. S. Wen et al, Teh, Proc. Conf. Rad. Curing ASIA, p478 Tokyo, October (1988).

Among these onium salts, diazonium salts are particularly preferable. Also, particularly preferable examples of these diazonium salts include those described in the publication of JP-A No. 5-158230.

Examples of the counter anion of the onium salt may include tetrafluoroboric acid, hexafluoroboric acid, triisopropylnaphthalenesulfonic acid, 5-nitro-o-toluenesulfonic acid, 5-sulfosalicylic acid, 2,5-dimethylbenzenesulfonic acid, 2,4,6-trimethylbenzenesulfonic acid, 2-nitrobenzenesulfonic acid, 3-chlorobenzenesulfonic acid, 3-bromobenzenesulfonic acid, 2-fluorocaprylnaphthalenesulfonic acid, dodecylbenzenesulfonic acid, 1-naphthol-5-sulfonic acid, 2-methoxy-4-hydroxy-5-benzoyl-benzenesulfonic acid and paratoluenesulfonic acid. Among these counter anions, particularly hexafluorophosphoric acid and alkyl aromatic sulfonic acids such as triisopropylnaphthalenesulfonic acid and 2,5-dimethylbenzenesulfonic acid are preferable.

Preferable examples of quinonediazides may be o-quinonediazide compounds. o-Quinonediazide compounds to be used in the invention are compounds having at least one o-quinonediazide group, which compounds are increased in alkali solubility by heat decomposition and various compounds may be used. o-Quinonediazide is thermally decomposed to lose the ability of inhibiting the dissolution of a binder and itself is changed to an alkali-soluble material. Namely, o-quinonediazide promotes the solubility of light-sensitive materials by these two effects. As the o-quinonediazide compound to be used in the invention, for example compounds described in J. Koser "Light-sensitive Systems" (John Wiley & Sons. Inc.) pp339–352 may be used and particularly sulfonates or sulfonic acid amides of o-quinonediazide obtained by reacting the o-quinonediazide compound with various aromatic polyhydroxy compounds or aromatic amino compounds are preferable. Also, esters of benzoquinone-(1,2)diazidosulfonic acid chloride or naphthoquinone-(1,2)-diazido-5-sulfonic acid chloride and a pyrogallol-acetone resin as described in the publication of JP-B No. 43-28403 and esters of benzoquinone-(1,2)-diazidosulfonic acid chloride or naphthoquinone-(1,2)-diazido-5-sulfonic acid chloride and a phenol-formaldehyde resin as described in U.S. Pat. Nos. 3,046,120 and 3,188,210 are preferably used.

Moreover, esters of naphthoquinone-(1,2)-diazido-4-sulfonic acid chloride and a phenol-formaldehyde resin or cresol-formaldehyde resin and esters of naphthoquinone-(1, 2)-diazido-4-sulfonic acid chloride and a pyrogallol-acetone resin are preferably used. Other useful o-quinonediazide compounds have been reported in many patents and used. Examples of these compounds include those described in each specification of JP-A Nos. 47-5303, 48-63802, 48-63803, 48-96575, 49-38701, 48-13354, JP-B Nos. 41-11222, 45-9610, 49-17481, U.S. Pat. Nos. 2,797,213, 3,454,400, 3,544,323, 3,573,917, 3,674,495, 3,785,825, U.K. Patent Nos. 1,227,602, 1,251,345, 1,267,005, 1,329, 888, 1,330,932 and German patent No. 854,890.

The amount of o-quinonediazide compound to be added is in a range preferably 1 to 50% by weight, more preferably 5 to 30% by weight and particularly preferably 10 to 30% by weight based on the total solid of the printing plate material. These compounds may be used singly, but may be used as a mixture of various types.

The amount of the additives other than o-quinonediazide compound is preferably 1 to 50% by weight, more preferably 5 to 30% by weight and particularly preferably 10 to 30% by weight. The additives and the binder in the invention are preferably contained in the same layer.

Also, cyclic acid anhydrides, phenols and organic acids may be further used together to improve sensitivity. As the cyclic acid anhydride, phthalic acid anhydride, tetrahydrophthalic acid anhydride, hexahydrophthalic acid anhydride, 3,6-endoxy-Δ4-tetrahydrophthalic acid anhydride, tetrachlorophthalic acid anhydride, maleic acid anhydride, chloromaleic acid anhydride, α-phenylmaleic acid anhydride, succinic acid anhydride and pyromellitic acid anhydride which are described in the specification of U.S. Pat. No. 4,115,128 may be used. As examples of the phenols, bisphenol A, p-nitrophenol, p-ethoxyphenol, 2,4,4'-trihydroxybenzophenone, 2,3,4-trihydroxybenzophenone, 4-hydroxybenzophenone, 4,4',4"-trihydroxytriphenylmethane, 4,4',3",4"-tetrahydroxy-3,5,3', 5'-tetramethyltriphenylmethane are given. Further, examples of the organic acids include sulfonic acids, sulfinic acids, alkylsulfuric acids, phosphonic acids, phosphates and carboxylic acids as described in each publication of JP-A Nos. 60-88942, 2-96755 and the like. Specific examples of these acids include p-toluenesulfonic acid, dodecylbenzenesulfonic acid, p-toluenesulfinic acid, ethylsulfuric acid, phenylphosphonic acid, phenylphosphinic acid, phenyl phosphate, diphenyl phosphate, benzoic acid, isophthalic acid, adipic acid, p-toluylic acid, 3,4-dimethoxybenzoic acid, phthalic acid, terephthalic acid, 4-cyclohexene-1,2-dicarboxylic acid, erucic acid, lauric acid, n-undecanoic acid and ascorbic acid. The proportion occupied by the cyclic acid anhydride, phenols and organic acids in the printing plate material is preferably 0.05 to 20% by weight, more preferably 0.1 to 15% by weight and particularly preferably 0.1 to 10% by weight.

Also, nonionic surfactants as described in the publication of JP-A Nos. 62-251740 and 3-208514, amphoteric surfactants as described in the publication of JP-A Nos. 59-121044 and 4-13149, siloxane compounds as described in the publication of European Patent No. 950,517 and copolymers of fluorine-containing monomers as described in JP-A No. 11-288093 may be added to the image forming layer coating solution according to the invention.

Specific examples of the nonionic surfactant include sorbitan tristearate, sorbitan monopalmitate, sorbitan triorate, stearic acid monoglyceride and polyoxyethylene nonylphenyl ether. Specific examples of the amphoteric surfactant include alkyldi(aminoethyl)glycine, alkylpolyaminoethylglycine hydrochloride, 2-alkyl-N-carboxyethyl-N-hydroxyethylimidazoliniumbetaine and N-tetradecyl-N,N-betaine compound (e.g., trademark: "Amorgen K", manufactured by Dai-ichi Kogyo Co.).

As the siloxane compound, a block copolymer of dimethylsiloxane and polyalkylene oxide is preferable. Specific examples of the siloxane compound may include polyalkylene oxide-modified silicone such as DBE-224, DBE-621, DBE-712, DBP-732 and DBP-534 manufactured by Chisso Corporation and Tego Glide 100 manufactured by Tego in Germany.

The proportion occupied by the nonionic surfactant and amphoteric surfactant in the printing plate material is preferably 0.05 to 15% by weight and more preferably 0.1 to 5% by weight.

A print-out agent for obtaining a visible image just after heating by exposure and dyes or pigments used as image colorants may be added in the image forming layer according to the invention.

Typical examples of the print-out agent may include a combination of a compound which releases an acid by the heat resulted from exposure and an organic dye capable of forming a salt. Specific examples of the combination may include combinations of o-naphthoquinonediazido-4-sulfonic acid halogenide and a salt-formable organic dye as described in each publication of JP-A Nos. 50-36209 and 53-8128 and combinations of a trihalomethyl compound and a salt-formable organic dye as described in each publication of JP-A Nos. 53-36223, 54-74728, 60-3626, 61-143748, 61-151644 and 63-58440. Examples of such a trihalomethyl compound include oxazole compounds and triazine compounds, which both have superior stability with time and give a clear print-out image.

As the colorant for an image, other dyes besides the salt-formable organic dyes may be used. As preferable examples of the dyes including these salt-formable organic dyes include oil-soluble dyes and basic dyes. Specific examples of these dyes may include Oil Yellow #101, Oil Yellow #103, Oil Pink #312, Oil Green BG, Oil Blue BOS, Oil Blue #603, Oil Black BY, Oil Black BS, Oil Black T-505 (these products are manufacture by Orient Chemical Industries, Ltd.), Victoria Pure Blue, Crystal Violet (CI42555), Methyl Violet (CI42535), Ethyl Violet, Rhodamine B (CI145170B), Malachite Green (CI42000) and Methylene Blue (CI52015). Also, dyes described in the publication of JP-A No. 62-293247 are particularly preferable. These dyes may be added to the printing plate material in an amount 0.01 to 10% by weight and preferably 0.1 to 3% by weight based on the total solid of the printing plate material. Moreover, a plasticizer may be compounded in the printing plate material of the invention according to the need to impart, for example, the flexibility to a film. For example, oligomers or polymers of butylphthalyl, polyethylene glycol, tributyl citrate, diethyl phthalate, dibutyl phthalate, dihexyl phthalate, dioctyl phthalate, tricresyl phosphate, tributyl phosphate, trioctyl phosphate, tetrahydrofurfuryl oleate and acrylic acid or methacrylic acid are used.

Besides the additives, epoxy compounds, vinyl ethers, phenol compounds having a hydroxymethyl group and phenol compounds having a alkoxymethyl group as described in the publication of JP-A No. 8-276558 and cross-linkable compounds having an alkali-dissolution inhibitive function as described in JP-A No. 11-160860 which has been previously proposed by the inventors of the invention may be properly added according to the purpose.

The image forming material of the invention comprises the above-mentioned image forming layer on an appropriate substrate and are applicable in various uses such as planographic printing plate precursors, color-proofs and display materials, and particularly is useful for a heat mode type planographic printing plate precursor enabling direct platemaking by exposure using an infrared laser.

A specific embodiment will be hereinafter explained by giving a case of applying the image forming material of the invention to a planographic printing plate precursor.

The planographic printing plate precursor according to the invention may be produced by applying a coating solution for a light-sensitive layer (image forming layer) and a solution, obtained by dissolving components for coating solutions of desired layers in a solvent, on an appropriate substrate. Also, a protective layer, a resin intermediate layer, a back-coat layer and the like may be formed according to the need.

Examples of the solvent used here may include, though not limited to, ethylene dichloride, cyclohexanone, methyl ethyl ketone, methanol, ethanol, propanol, ethylene glycol monomethyl ether, 1-methoxy-2-propanol, 2-methoxyethyl acetate, 1-methoxy-2-propyl acetate, dimethoxyethane, methyl lactate, ethyl lactate, N,N-dimethylacetamide, N,N-dimethylformamide, tetramethylurea, N-methylpyrrolidone, dimethylsulfoxide, sulfolane, γ-butyrolactone and toluene. These solvents are used either singly or by mixing them.

The concentration of the components (total content including the additives) in the solvent is 1 to 50% by weight.

The coating amount (solid content) on the substrate after applying and drying is preferably 0.5 to 5.0 $g/m^2$ in general in the case of the image forming layer of the planographic printing plate precursor though it depends on the use. With an increase in the coating amount, apparent sensitivity is heightened, but the film characteristics of the image forming layer is lowered.

Various methods may be used as the coating method and examples of these methods may include bar coater coating, rotational coating, spray coating, curtain coating, dip coating, air knife coating, blade coating and roll coating.

Surfactants for bettering coatability, for example, fluorine-containing surfactants as described in the publication of JP-A No. 62-170950 may be compounded in the image forming layer of the invention. The amount of the surfactant is preferably 0.01 to 1% by weight and more preferably 0.05 to 0.5% by weight based on the total solid of the image forming layer.

Resin Intermediate Layer

The planographic printing plate precursor may be provided with a resin intermediate layer between the image forming layer and the substrate according to the need.

With the provision of this resin intermediate layer, the image forming layer which is an infrared sensible layer improved in solubility in an alkali developing solution by exposure is positioned on or close to the exposed surface, whereby the sensitivity to an infrared laser is bettered. Also, the provision of the resin intermediate layer has such an advantage that the resin intermediate layer consisting of a polymer exists between the image forming layer and the substrate and functions as an insulating layer, so that the heat generated by exposure is not diffused to the substrate and used efficiently for the formation of an image, thereby attaining high sensitization. Also, in the unexposed portion, the image forming layer, which prevents the penetration of an alkali developing solution, itself functions as a protective layer for protecting the resin intermediate layer and therefore the developing stability is bettered and an image superior in discrimination is formed and also, it is considered that the stability with time is secured. On the other hand, in the exposed portion, the components of the image forming layer whose dissolution inhibition ability is dissolved is promptly dissolved in a developing solution, dispersed. Further, because the resin intermediate layer present adjacent to the substrate itself is constituted of an alkali-soluble polymer, it has high solubility in a developing solution and therefore it dissolves promptly without generating a residual film, even in the case of using a developing solution reduced in activity, which also contributes to an improvement in developing ability and this resin intermediate layer is therefore considered to be useful.

Substrate

Examples of the substrate used in the invention include dimensionally stable plate materials, such as paper, paper laminated with plastic (e.g., polyethylene, polypropylene and polystyrene), metal plates (e.g., aluminum, zinc and copper), plastic films (e.g., cellulose diacetate, cellulose triacetate, cellulose propionate, cellulose butyrate, cellulose acetate butyrate, cellulose nitrate, polyethylene terephthalate, polyethylene, polystyrene, polypropylene, polycarbonate and polyvinylacetal), paper or plastic films on which metals as mentioned above are laminated or deposited.

The substrate used in the invention is preferably a polyester film or an aluminum plate when it is used for a planographic printing plate precursor. Among these materials, an aluminum plate which has high dimensional stability and is relatively inexpensive is particularly preferable. A preferable aluminum plate is a pure aluminum plate and an alloy plate containing aluminum as major components and a trace amount of foreign elements and also, may be a plastic film on which aluminum is laminated or deposited. Examples of the foreign elements contained in the aluminum alloy include silicon, iron, manganese, copper, magnesium, chromium, zinc, bismuth, nickel and titanium. The content of these foreign elements in the alloy is 10% by weight or less. Particularly preferable aluminum in the invention is pure aluminum. However, it is difficult to produce perfectly pure aluminum from the viewpoint of refining technologies and therefore the aluminum plate may contain trace foreign elements.

As aforementioned, the composition of the aluminum plate applied to the invention is not specified and aluminum plates which have been well known and commonly used may be used appropriately. The thickness of the aluminum plate used in the invention is about 0.1 mm to 0.6 mm, preferably 0.15 mm to 0.4 mm and particularly preferably 0.2 mm to 0.3 mm.

Prior to the roughing of the aluminum plate, degreasing treatment using surfactants, organic solvents or an aqueous alkaline solution is carried out to remove rolling oil on the surface as desired. The surface roughing treatment of the surface of the aluminum plate is carried out by various methods. For example, the surface roughing treatment is carried out using a method in which a surface is roughened mechanically, a method in which a surface is electrochemically roughened by melting the surface or a method in which a surface is selectively melted chemically. As the mechanical method, a known method such as a polishing method which uses balls, brushing, blasting or buffing may be used. Also, as the electrochemical surface roughing method, there is a method in which a surface is roughened using d.c. current or a.c. current in hydrochloric acid or nitric acid electrolyte. Also, as disclosed in the publication of JP-A No. 54-63902, a method for which the both are combined may be utilized. The aluminum plate which is surface-roughened in this manner is subjected to alkali etching treatment and neutralizing treatment as required and then to anodic oxidation treatment as desired to heighten the moisture-retentivity and wear resistance of the surface. As the electrolyte used for the anodic oxidation treatment of the aluminum plate, it is possible to use various electrolytes which form a porous oxidation film and sulfuric acid, phosphoric acid, oxalic acid, chromic acid or a mixture of these acids is used in general. The concentration of the electrolyte is properly determined by the type of electrolyte.

General treating conditions of the anodic oxidation are preferably in the following ranges though they can be unspecified as a whole because they differ depending on the type of electrolyte: concentration of the electrolyte: 1 to 80% by weight solution, solution temperature: 5 to 70° C., current density: 5 to 60 A/dm$^2$, voltage: 1 to 100 V and electrolyzation time: 10 seconds to 5 minutes. When the amount of the anodic oxidation film is less than 1.0 g/m$^2$, insufficient printing durability is obtained and the non-image portion of the planographic printing plate is easily dmaged, so that a so-called "damage stain", that is, a phenomenon that ink is stuck to the damaged portion during printing, tends to occur. After the anodic oxidation treatment is performed, the surface of the aluminum is made hydrophilic according to the need. As the method for making an aluminium surface hydrophilic, there is an alkali metal silicate (e.g., aqueous sodium silicate solution) method such as those described in U.S. Pat. No. 2,714,066, U.S. Pat. No. 3,181,461, U.S. Pat. No. 3,280,734 and U.S. Pat. No. 3,902,734. In this method, the substrate is dipped in an aqueous sodium silicate solution and, if necessary, is electrified. Besides the above treatment, methods in which the substrate is treated with potassium fluorozirconate as disclosed in the publication of JP-B No. 36-22063 and a method in which the substrate is treated with polyvinylphosphonic acid as disclosed in U.S. Pat. Nos. 3,276,868, 4,153,461 and 4,689,272 are used.

The planographic printing plate precursor according to the invention has the positive image forming layer on the substrate and may be provided with an undercoat layer between the image forming layer and the substrate according to the need.

Various organic compounds are used as the components for the undercoat layer. The organic compound is selected from, for example, carboxymethyl cellulose, dextrin, gum arabic, phosphonic acids having an amino group such as 2-aminoethylphosphonic acid, organic phosphonic acids such as phenylphosphonic acid, naphthylphosphonic acid, alkylphosphonic acid, glycerophosphonic acid, methylenediphosphonic acid and ethylenediphosphonic acid, which may have a substituent, organic phosphoric acids such as phenylphosphoric acid, naphthylphosphoric acid, alkylphosphoric acid and glycerophosphoric acid, which may have a substituent, organic phosphinic acids such as phenylphosphinic acid, naphthylphosphinic acid, alkylphosphinic acid and glycerophosphinic acid, which may have a substituent, amino acids such as glycine and β-alanine and hydrochlorides of amine having a hydroxy group such as hydrochlorides of triethanolamine. These compounds may be used by mixing two or more.

This organic undercoat layer may be formed by a method in which a solution obtained by dissolving the organic compound in water or an organic solvent such as methanol, ethanol or methyl ethyl ketone or a mixture of these solvents is applied to the aluminum plate and dried or by a method in which the aluminum plate is dipped in a solution obtained by dissolving the organic compound in water or an organic solvent such as methanol, ethanol and methyl ethyl ketone or a mixture of these solvents to make the compounds adsorb to the aluminum plate, which is then washed with water or the like and dried. In the former method, a solution in which the concentration of the organic compound is 0.005 to 10% by weight may be applied using various methods. Also, in the latter method, the concentration of the solution is 0.01 to 20% by weight and preferably 0.05 to 5% by weight, the dipping temperature is 20 to 90° C. and preferably 25 to 50° C. and the dipping time is 0.1 seconds to 20 minutes and preferably 2 seconds to 1 minute. The solution to be used for this may be adjusted to pH 1 to 12 by using a basic material such as ammonia, triethylamine or potassium hydroxide and an acidic material such as hydrochloric acid or phosphoric acid. Also, a yellow dye may be added to improve the reproducibility of the tone of the image forming material.

The amount of the organic undercoat layer to be applied is properly 2 to 200 mg/m$^2$ and preferably 5 to 100 mg/m$^2$. If the above amount to be applied is less than 2 mg/m$^2$, sufficient printing durability is not obtained. Also, even if the amount is greater than 200 mg/M$^2$, the same result is obtained.

The positive planographic printing plate precursor produced in the above manner is usually subjected to an image exposure process and developing treatment.

As a light source of the rays used for image exposure, light sources having emitting wavelength in a range from the near-infrared region to the infrared region are preferable and a solid laser and a semiconductor laser are particularly preferable.

As a developing solution and a replenishing solution used in the production of the planographic printing plate of the invention, a conventionally known aqueous alkali solution may be used.

Examples of the alkali include inorganic alkali salts such as sodium silicate, potassium silicate, sodium tertiary phosphate, potassium tertiary phosphate, ammonium tertiary phosphate, sodium secondary phosphate, potassium secondary phosphate, ammonium secondary phosphate, sodium carbonate, potassium carbonate, ammonium carbonate, sodium bicarbonate, potassium bicarbonate, ammonium bicarbonate, sodium borate, potassium borate, ammonium borate, sodium hydroxide, ammonium hydroxide, potassium hydroxide and lithium hydroxide. Also, organic alkali agents such as monomethylamine, dimethylamine, trimethylamine, monoethylamine, diethylamine, triethylamine, monoisopropylamine, diisopropylamine, triisopropylamine, n-butylamine, monoethanolamine, diethanolamine, triethanolamine, monoisopropanolamine, diisopropanolamine, ethyleneimine, ethylenediamine and pyridine may be used. These alkali agents are used either singly or in combinations of two or more.

Particularly preferable developing solutions among these alkali agents are aqueous solutions of silicates such as sodium silicate and potassium silicate. The reason is that developing ability can be controlled by the ratio and concentrations of silicon oxide SiO$_2$ which is a component of the silicate and an alkali metal oxide M$_2$O. Alkali metal silicates as described in the publication of JP-A No. 54-62004 and JP-B No. 57-7427 are used efficiently.

Further, in the case of developing using an automatic developing machine, it is known that a large number of PS plates can be treated without exchanging a developing solution in a developing tank for a long period of time by adding an aqueous solution (replenishing solution) having higher alkalinity than the developing solution to the developing solution. This replenishing system is also preferably applied to the invention. Various surfactants and organic solvents may be added as required to the developing solution and the replenishing solution with the intention of promoting and restricting developing ability, dispersing developing scum and improving the affinity of the printing plate image portion to ink.

Preferable examples of the surfactant include anionic, cationic, nonionic or amphoteric surfactants. Reducing agents such as sodium salts and potassium salts of inorganic acids such as hydroquinone, resorcinol, sulfurous acid, sulfurous acid hydroacid and further, organic carboxylic acid, antifoaming agents and water softeners may be added to the developing solution and to the replenishing solution according to the need.

The printing plate which has been developed using the foregoing developing solution and replenishing solution is subjected to after treatment using rinsing water, a rinsing solution containing surfactants and the like and a desensitizing solution containing gum arabic and a starch derivative. These treatments may be used in various combinations for the after treatment in the case of using the image recording material of the invention as a printing plate.

In plate-making and printing fields in recent years, an automatic developing machine for printing plates has been widely used for rationalization and standardization of plate-making works. This automatic developing machine usually consists of a developing section and an after treating section, comprising a unit for carrying a printing plate, vessels for each processing solution and a spraying unit, wherein each processing solution which is pumped up is sprayed from a spray nozzle while carrying the exposed plating plate horizontally to carry out developing treatment. Also, a method has been known recently in which a printing plate is carried by an in-liquid guide roll while dipping it in a processing solution vessel filled with a processing solution. In such an automatic treatment, the printing plate can be treated while supplying a replenishing solution to each processing solution corresponding to a throughput and operating time. Also, a treating system may be applied in which treatment is carried out using a substantially unused process solution as a disposable.

When there is an image portion (for example, a film edge trace on a original picture film) unnecessary for a planographic printing plate obtained through image exposure, developing, washing with water or rinsing and/or application of gum in the planographic printing plate precursor according to the invention, the unnecessary image portion is erased. Such erasure is preferably carried out using a method in which an erasing solution such as those described in the publication of JP-B No. 2-13293 is applied to the unnecessary image portion, which is then allowed to stand for a predetermined time and then washed with water. A method in which active rays propagated through an optical fiber as described in the publication of JP-A No. 59-174842 is applied to the unnecessary image portion and then developing treatment is performed may be utilized.

The planographic printing plate obtained in the above manner may be subjected to a printing step after desensitizing gum is applied to the plate. In the case of intending to produce a planographic printing plate having higher printing durability, burning treatment is carried out. When the planographic printing plate is subjected to burning, it is preferably subjected to treatment using a surface regulating solution such as those described in each publication of JP-B Nos. 61-2518, 55-28062, JP-A Nos. 62-31859 and 61-159655 prior to burning.

A method in which the solution is applied to the planographic printing plate either by using sponge or absorbent cotton impregnated with the solution or by dipping the printing plate in a vat filled with the surface regulating solution or a method in which the surface regulating solution is applied using an automatic coater is applied to the treatment using the surface regulating solution. Also, after applying the surface regulation solution, the amount of the solution per unit area may be uniformed by a squeegee or a squeegee roller. This operation brings about more preferable result.

The amount of the surface regulating solution to be applied is appropriately 0.03 to 0.8 g/m$^2$ (dry weight). The planographic printing plate to which the surface regulating solution has been applied is heated by, for example, a burning processor (for example, Burning Processor: "BP-1300", commercially available from Fuji Photo Film Co., Ltd.) after it is dried as required. The heating temperature and heating time in this case are in a range from 180 to 300° C. and in a range from 1 to 20 minutes respectively though they differ depending on the type of component forming an image.

The planographic printing plate which has been subjected to burning treatment may be processed optionally by treatments which have been performed so far, such as washing with water and application of gum. However, in the case where a surface regulating solution containing a water-soluble high molecular compound has been used, a so-called desensitizing treatment such as application of gum may be omitted. The planographic printing plate obtained by such treatments as mentioned above is subjected to, for example, an offset printer and used for making a large number of prints.

EXAMPLES

Examples 1 to 18
Production of a Substrate

Aluminum plates (material 1050) having a thickness of 0.3 mm were washed with trichloroethylene to degrease it. Then, the surface of the aluminum plates was pebbled using a nylon brush and a 400 mesh pumice-water suspension, followed by thoroughly washing with water. These plates were soaked in an aqueous 25% sodium hydroxide solution kept at 45° C. for 9 seconds to carry out etching and then washed with water. After that, the plates were further soaked in 20% nitric acid for 20 seconds, followed by washing with water. The amount of etching on the pebbled surface at this time was about 3 g/m$^2$. Next, an anodic oxidation film was formed on these plates on conditions that 7% sulfuric acid was used as an electrolyte and that a current density was 15 A/dm$^2$. The amount of the anodic oxidation film was 3 g/m$^2$. The plates were then washed with water, dried and further treated using an aqueous solution containing 2.5% by weight of sodium silicate at 30° C. for 10 seconds. Then, the following undercoat solution 1 was applied to the plates and the coating film was dried at 80° C. for 15 seconds. The coating amount of the film after dried was 15 mg/m$^2$.

<Undercoat Solution 1>

| | |
|---|---|
| Copolymer described below and having a molecular weight of 28,000 | 0.3 g |
| Methanol | 100 g |
| Water | 1 g |

Synthesis of a Copolymer 1

A 500 ml three-neck flask equipped with a stirrer, a cooling tube and a dropping funnel was charged with 31.0 g (0.36 mol) of methacrylic acid, 39.1 g (0.36 mol) of ethyl chloroformate and 200 ml of acetonitrile and the mixture was stirred under cooling in an ice bath. To the mixture was added dropwise 36.4 g (0.36 mol) triethylamine over about one hour by using the dropping funnel. After the dropwise addition was finished, the ice bath was taken away and the mixture was stirred at ambient temperature for 30 minutes.

To the reaction mixture was added 51.7 g (0.30 mol) of p-aminobenzenesulfonamide and the mixture was stirred for one hour under heating at 70° C. in an oil bath. After the reaction was finished, the mixture was poured into 1 liter of water with stirring the water and the resulting mixture was stirred for 30 minutes. The mixture was subjected to filtration to collect the precipitates, which were then made into a slurry by adding 500 ml of water. The slurry was then subjected to filtration and the resulting solid was dried to obtain a white solid of N-(p-aminosulfonylphenyl) methacrylamide (yield: 46.9 g).

Next, a 20 ml three-neck flask equipped with a stirrer, a cooling tube and a dropping funnel was charged with 4.61 g (0.0192 mol) of N-(p-aminosulfonylphenyl) methacrylamide, 2.58 g (0.0258 mol) of ethyl methacrylate, 0.80 g (0.015 mol) of acrylonitrile and 20 g of N,N-dimethylacetamide and the mixture was stirred under heating at 65° C. in a hot water bath. To the mixture was added 0.15 g of "V-65" (manufactured by Wako Pure Chemical Industries, Ltd.) and the mixture was stirred for 2 hours in a nitrogen stream while keeping the mixture at 65° C. To this reaction mixture was further added a mixture of 4.61 g of N-(p-aminosulfonylphenyl)methacrylamide, 2.58 g of methylmethacrylate, 0.80 g of acrylonitrile, 20 g of N,N-dimethylacetamide and 0.15 g of "V-65" over 2 hours by using the dropping funnel. After the dropwise addition was finished, the resulting mixture was further stirred for 2 hours at 65° C. After the reaction was finished, 40 g of methanol was added to the mixture, which was then cooled and the resulting mixture was poured into 2 liter of water with stirring the water. The mixture was stirred for 30 minutes and then the precipitates were collected by filtration and dried to obtain 15 g of a white solid. The weight average molecular weight (polystyrene standard) of this specified copolymer 1 was measured by gel permeation chromatography to find that it was 54,000.

Production of Planographic Printing Plate Precursors

The following image forming layer coating solution 1 was applied to the resulting substrates and dried at 130° C. for one minute to form a lower image forming layer. The coating amount after the coating film was dried was 1.3 g/m$^2$.

<Lower Layer Coating Solution 1>

| | |
|---|---|
| Copolymer 1 described above | 0.75 g |
| Infrared absorbent 1 (light-heat converting agent: the following structure) | 0.02 g |
| p-Toluenesulfonic acid | 0.002 g |
| Tetrahydrophthalic acid anhydride | 0.05 g |
| Dye obtained from Victoria Pure Blue BOH by using a 1-naphthalenesulfonic acid anion for its counter anion | 0.015 g |
| Fluorine-containing surfactant (Megafac F-177, manufactured by Dainippon Ink and Chemicals, Incorporated) | 0.02 g |
| γ-butyrolactone | 8 g |
| Methyl ethyl ketone | 7 g |
| 1-Methoxy-2-propanol | 7 g |

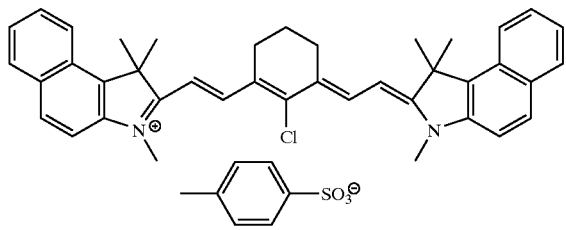

Then, the following image forming layer coating solution 2 was applied to the lower image forming layer and dried at 120° C. for one minute to form an upper image forming layer, and then planographic printing plate precursors of Examples 1 to 18 were obtained. The total coating amount of the image forming layer coating solution after the coating film was dried was 1.8 g/m².

<Image Forming Layer Coating Solution 2>

| | |
|---|---|
| Novolac resin (m/p = 6/4, Mw = 4000) | 0.8 g |
| Infrared absorbent 1 | 0.03 g |
| Compound represented by the general formula (1) (compound described in Table 1) | 0.04 g |
| Dye obtained from Victoria Pure Blue BOH by using a 1-naphthalenesulfonic acid anion for its counter anion | 0.015 g |
| Fluorine-containing surfactant (Megafac F-177, manufactured by Dainippon Ink and Chemicals, Incorporated) | 0.02 g |
| Methyl ethyl ketone | 10 g |
| 1-Methoxy-2-propanol | 5 g |

Comparative Example 1

A planographic printing plate precursor was obtained in the same manner as in the above Example except that a coating solution was used which was prepared by excluding the compound represented by the general formula (1) from the image forming coating solution 2 used for the upper image forming layer.

Comparative Example 2

A planographic printing plate precursor was obtained in the same manner as in the above Example except that a coating solution was used which was prepared by compounding an ammonium compound (ammonium A) having the following structure in place of the compound represented by the general formula (1) in the image forming coating solution 2 used for the upper image forming layer.

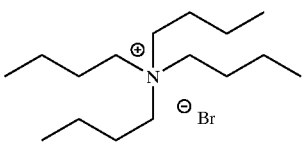

Evaluation of Planographic Printing Plate Precursors

Each resulting planographic printing plate precursors were evaluated according to the following method. The results of evaluation are shown in Table 1.

1. Sensitivity

The resulting planographic printing plate precursors were exposed using a Trend Setter 3244 (manufactured by CREO Co., Ltd.) and developed using DT-1 (solution diluted with water at a dilution of 1:8). At this time, the exposure was performed at different exposure amounts and a minimum exposure amount required to develop the exposed portions sufficiently under the same developing condition was defined as "sensitivity". The sensitivity is rated higher as the value is lower.

2. Anti-Scratching Characteristics

The anti-scratching characteristics were evaluated by a rubbing test using absorbent cotton. Using absorbent cotton, the surface of the image forming layer was rubbed under a fixed force. The anti-scratching characteristics were determined by the number of rubbings when the unexposed portion was completely removed as a result of the rubbing using the absorbent cotton. In this evaluation, the test was made using 5 samples and an average of the numbers of rubbings of five samples was adopted (maximum: 20 times).

3. Developing Latitude

The planographic printing plate precursors which had been exposed at an exposure amount of 188 mJ/cm² by using a Trend Setter 3244 (manufactured by CREO Co., Ltd.) were developed using a developing solution prepared by properly diluting the undiluted solution of the DT-1 and by adjusting the electroconductivity (mS: milli-siemens). At this time, an electroconductivity at which the exposed portions were sufficiently removed and the very limit of an electroconductivity at which the unexposed portions were decreased in film thickness were measured and a difference (electroconductivity width) between these electroconductivities was defined as the index of the developing latitude. The larger the difference is, the higher the developing latitude is rated.

TABLE 1

| | Compound of the general formula (1) | Sensitivity | Anti-scratching characteristics | Developing latitude |
|---|---|---|---|---|
| Example 1 | I-2 | 125 | 20 | 18 |
| Example 2 | I-3 | 130 | 20 | 18 |
| Example 3 | I-10 | 125 | 20 | 16 |
| Example 4 | I-7 | 130 | 20 | 16 |
| Example 5 | I-23 | 133 | 20 | 18 |
| Example 6 | I-35 | 115 | 20 | 16 |
| Example 7 | I-42 | 133 | 20 | 16 |
| Example 8 | I-54 | 133 | 20 | 18 |
| Example 9 | II-6 | 133 | 20 | 16 |
| Example 10 | II-15 | 133 | 20 | 18 |
| Example 11 | III-9 | 133 | 20 | 16 |
| Example 12 | III-13 | 133 | 20 | 16 |
| Example 13 | IV-3 | 110 | 20 | 18 |
| Example 14 | IV-14 | 125 | 20 | 16 |
| Example 15 | V-2 | 133 | 20 | 16 |
| Example 16 | V-13 | 133 | 20 | 18 |

TABLE 1-continued

| | Compound of the general formula (1) | Sensitivity | Anti-scratching characteristics | Developing latitude |
|---|---|---|---|---|
| Example 17 | V-17 | 135 | 20 | 18 |
| Example 18 | V-20 | 133 | 20 | 16 |
| Comparative Example 1 | none | 133 | 8 | 8 |
| Comparative Example 2 | Ammonium A | 188 | 20 | 1 |

As shown in Table 1, it is understood that each planographic printing plate precursor of Examples 1 to 18 to which the image forming material of the present invention is applied attains high sensitization while maintaining a high level of developing latitude and anti-scratching characteristics. On the other hand, the planographic printing plate precursor of Comparative Example 1 to which the specified ammonium compound used in the invention was not added exhibited low anti-scratching characteristics and was inferior in developing latitude though it enables highly sensitive recording. The planographic printing plate precursor of the comparative example 2 to which a known ammonium compound which can strongly interact with the alkali-soluble resin is inferior in sensitivity and developing latitude though it exhibits excellent anti-scratching characteristics. These planographic printing plate precursors of the comparative examples are on a practically problematic level.

Examples 19 to 26

The following image forming layer coating solution 3 was applied to the same substrates that were used in Example 1 such that the coating amount after the solution was dried was 1.2 g/m² to obtain planographic printing plate precursors.

<Image Forming Layer Coating Solution 3>

| | |
|---|---|
| Fluorine-containing polymer (the following structure) | 0.03 g |
| Copolymer 1 | 0.75 g |
| Novolac resin (m/p = 6/4, Mw = 4000) | 0.20 g |
| Compound represented by the general formula (1) (compound described in Table 2) | 0.05 g |
| Tetrahydrophthalic acid anhydride | 0.03 g |
| Pyrylium dye B (following structure) | 0.017 g |
| Dye obtained from Victoria Pure Blue BOH by using a 1-naphthalenesulfonic acid anion for its counter anion | 0.015 g |
| 3-Methoxy-4-diazodiphenylamine hexafluorophosphate | 0.02 g |
| n-Dodecyl stearate | 0.03 g |
| Fluorine-containing surfactant (Megafac F-177, manufactured by Dainippon Ink and Chemicals, Incorporated) | 0.05 g |
| γ-butyrolactone | 10 g |
| Methyl ethyl ketone | 10 g |
| 1-Methoxy-2-propanol | 8 g |

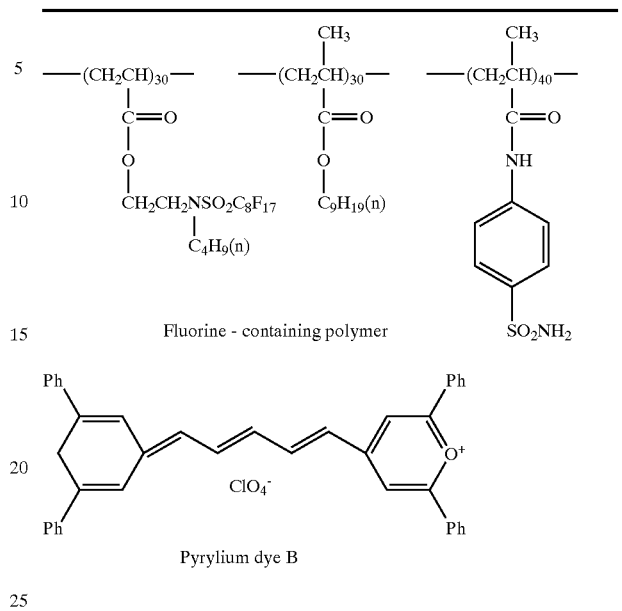

Fluorine - containing polymer

Pyrylium dye B

Comparative Example 3

A planographic printing plate precursor was obtained in the same manner as in the above Example except that a coating solution was used which was prepared by excluding the compound represented by the general formula (1) from the image forming coating solution 3.

Comparative Example 4

A planographic printing plate precursor was obtained in the same manner as in the above Example except that a coating solution was used which was prepared by compounding an ammonium compound (ammonium A) used in the Comparative Example 2 in place of the compound represented by the general formula (1) in the image forming coating solution 3.

Each resulting planographic printing plate precursor was evaluated in the same method as in Example 1. The results of evaluation are shown in Table 2.

TABLE 2

| | Compound of the general formula (1) | Sensitivity | Anti-scratching characteristics | Developing latitude |
|---|---|---|---|---|
| Example 19 | I-1 | 100 | 5.2 | 6 |
| Example 20 | I-3 | 100 | 4.8 | 6 |
| Example 21 | I-13 | 80 | 5.0 | 6 |
| Example 22 | I-31 | 80 | 4.8 | 6 |
| Example 23 | II-14 | 90 | 5.2 | 6 |
| Example 24 | III-3 | 90 | 4.6 | 6 |
| Example 25 | IV-9 | 100 | 6.0 | 6 |
| Example 26 | V-2 | 80 | 5.8 | 6 |
| Comparative Example 3 | none | 188 | 4.8 | 2 |
| Comparative Example 4 | Ammonium A | 90 | 1 | 4 |

As shown in Table 2, it is understood that like those having a recording layer with a multi layer structure, each planographic printing plate precursor of Examples 19 to 26 to which the image forming material of the invention is applied and which have a recording layer with a monolayer structure attains high sensitization while maintaining a high level of developing latitude and anti-scratching characteristics. On the other hand, the planographic printing plate precursor of Comparative Example 3 to which the specified ammonium compound used in the invention is not added exhibits low anti-scratching characteristics and is inferior in developing latitude. The planographic printing plate precursor of Comparative Example 4 to which an ammonium compound out of the scope of the invention is added is inferior in sensitivity and developing latitude. These planographic printing plate precursors of the comparative examples are on a practically problematic level.

Examples 27 to 34
Production of Planographic Printing Plate Precursors

The following image forming layer coating solution 4 was applied to the same substrates that were used in Example 1 and dried at 130° C. for one minute to form an image forming layer, thereby obtaining planographic printing plate precursors. The coating amount after the solution was dried was 1.3 g/m².

<Image Forming Layer Coating Solution 4>

| | |
|---|---|
| Novolac resin (cresol novolac with m-:p- = 6:4, and Mw = 4000) | 1.0 g |
| Compound represented by the general formula (1) (compound described in Table 3) | 0.05 g |
| Infrared absorbent (following structure) | 0.05 g |
| Dye obtained from Victoria Pure Blue BOH by using a 1-naphthalenesulfonic acid anion for its counter anion | 0.01 g |
| Fluorine-containing surfactant (Megafac F-177, manufactured by Dainippon Ink and Chemicals, Incorporated) | 0.05 g |
| γ-butyrolactone | 3.0 g |
| Methyl ethyl ketone | 8.0 g |
| 1-Methoxy-2-propanol | 7.0 g |

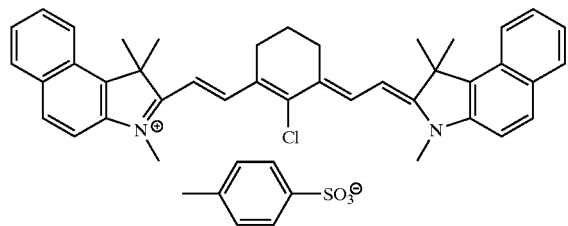

Comparative Example 5

A planographic printing plate precursor was obtained in the same manner as in the above Example except that a coating solution was used which was prepared by excluding the compound represented by the general formula (1) from the image forming coating solution 4.

Comparative Example 6

A planographic printing plate precursor was obtained in the same manner as in the above Example except that a coating solution was used which was prepared by compounding an ammonium compound (ammonium A) used in the Comparative Example 2 in place of the compound represented by the general formula (1) in the image forming coating solution 4.

Each resulting planographic printing plate precursor was evaluated in the same method as in Example 1. The results of evaluation are shown in Table 3.

TABLE 3

| | Compound of the general formula (1) | Sensitivity | Anti-scratching characteristics | Developing latitude |
|---|---|---|---|---|
| Example 27 | I-2 | 90 | 8.0 | 8 |
| Example 28 | I-12 | 90 | 8.2 | 8 |
| Example 29 | I-39 | 100 | 7.8 | 8 |
| Example 30 | I-45 | 90 | 8.0 | 8 |
| Example 31 | II-2 | 90 | 8.0 | 8 |
| Example 32 | III-13 | 90 | 7.8 | 8 |
| Example 33 | IV-10 | 100 | 8.2 | 8 |
| Example 34 | V-21 | 90 | 8.0 | 8 |
| Comparative Example 5 | none | 180 | 8.0 | 2 |
| Comparative Example 6 | Ammonium A | 100 | 2.4 | 6 |

As shown in Table 3, it is understood that like those having a recording layer with a multilayer structure, each planographic printing plate precursor of Examples 27 to 34 to which the image forming material of the invention is applied and which have a recording layer with a monolayer structure using the novolac resin attains high sensitization while maintaining a high level of developing latitude and anti-scratching characteristics. On the other hand, the planographic printing plate precursor of Comparative Example 5 to which the specified ammonium compound used in the invention is not added exhibits low anti-scratching characteristics and is inferior in developing latitude. The planographic printing plate precursor of Comparative Example 6 to which an ammonium compound out of the scope of the invention is added is inferior in sensitivity and developing latitude. These planographic printing plate precursors of the comparative examples are on a practically problematic level.

What is claimed is:

1. An image forming material comprising an image forming layer containing a water-insoluble and alkali-soluble resin, a light-heat converting agent and a compound represented by the following general formula (1):

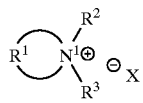

wherein $R^1$ to $R^3$ independently represent an organic group, where $R^1$ represents a residue forming a ring containing a $N^1$ atom, $R^2$ and $R^3$ may bond to each other to form a ring or at least one of $R^2$ and $R^3$ bonds to $R^1$ to form a ring and $X^-$ represents a conjugate base of an organic acid or inorganic acid.

2. An image forming material according to claim 1, wherein the ring formed by $R^1$ and the $N^1$ atom is a three- to ten-membered ring.

3. An image forming material according to claim 1, wherein the ring formed by $R^1$ and the $N^1$ atom contains a heteroatom other than the $N^1$ atom.

4. An image forming material according to claim 1, wherein $R^2$ and $R^3$ are independently selected from the group consisting of an alkyl group, an alkenyl group, an alkynyl group, an aryl group, an unsubstituted or substituted amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a sulfinyl group, a ureide group, phosphoric acid amide group, hydroxy group, a mercapto group, a halogen atom, a cyano group, a sulfo group, a carboxyl group, a nitro group, a hydroxamic acid group, a sulfino group, a hydrazino group, an imino group, a heterocyclic group and a silyl group.

5. An image forming material according to claim 4, wherein $R^2$ and $R^3$ are independently selected from the group consisting of an alkyl group, an alkenyl group, an alkynyl group and an aryl group.

6. An image forming material according to claim 1, wherein the compound represented by the general formula (1) is represented by the following general formula (1-a)

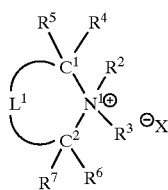

(1-a)

wherein $R^2$ and $R^3$ independently represent an organic group, $R^4$ to $R^7$ independently represent a hydrogen atom or a substituent and $R^4$ to $R^7$ may bond to each other to form a ring or may bond to $L^1$, $R^2$ and/or $R^3$ to form a ring, and when the $C^1$ carbon atom and the $C^2$ carbon atom form a double bond or a triple bond in combination with $L^1$, $R^4$ to $R^7$ may not be present corresponding to this, $L^1$ represents a polyvalent connecting group forming a ring containing —$C^1$—$N^1$—$C^2$— or a single bond and $X^-$ represents a conjugate base of an organic acid or an inorganic acid.

7. An image forming material according to claim 1, wherein the compound represented by the general formula (1) is represented by the following general formula (1-b)

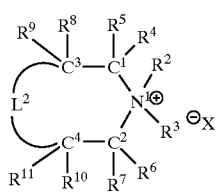

(1-b)

wherein $R^2$ and $R^3$ independently represent an organic group, $R^4$ to $R^{11}$ independently represent a hydrogen atom or a substituent and $R^4$ to $R^{11}$ may bond to each other to form a ring or may bond to $L^2$, $R^2$ and/or $R^3$ to form a ring, and when the $C^3$ carbon atom and the $C^4$ carbon atom form a double bond or a triple bond in combination with the $C^1$ carbon atom and the $C^2$ carbon atom respectively, when the $C^3$ carbon atom and $C^4$ carbon atom form a double bond or a triple bond in combination with $L^2$ and when $L^2$ represents a double bond connecting the $C^3$ carbon atom with the $C^4$ carbon atom, $R^4$ to $R^{11}$ may not be present corresponding to this, $L^2$ represents a polyvalent connecting group forming a ring containing —$C^3$—$C^1$—$N^1$—$C^2$—$C^4$— or a single bond or double bond connecting $C^3$ with $C^4$ and $X^-$ represents a conjugate base of an organic acid or inorganic acid.

8. An image forming material according to claim 1, wherein the compound represented by the general formula (1) is represented by the following general formula (1-c)

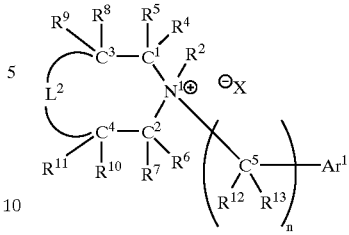

(1-c)

wherein $R^2$ represents an organic group, $R^4$ to $R^{13}$ independently represent a hydrogen atom or a substituent and $R^4$ to $R^{13}$ may bond to each other to form a ring or may bond to $L^2$ and/or $R^2$ to form a ring, and when the $C^3$ carbon atom and the $C^4$ carbon atom form a double bond or a triple bond in combination with the $C^1$ carbon atom and the $C^2$ carbon atom respectively, when the $C^3$ carbon atom and $C^4$ carbon atom form a double bond or a triple bond in combination with $L^2$ and when $L^2$ represents a double bond connecting the $C^3$ carbon atom with the $C^4$ carbon atom, $R^4$ to $R^{11}$ may not be present corresponding to this, $Ar^1$ represents an aromatic ring and may bond to $L^2$, $R^2$ and/or $R^4$ to $R^{13}$ to form a ring, n denotes 0 or a positive integer, $L^2$ represents a polyvalent connecting group forming a ring containing —$C^3$—$C^1$—$N^1$—$C^2$—$C^4$— or a single bond or double bond connecting $C^3$ with $C^4$ and $X^-$ represents a conjugate base of an organic acid or inorganic acid.

9. An image forming material according to claim 1, wherein the compound represented by the general formula (1) is represented by the following general formula (1-d)

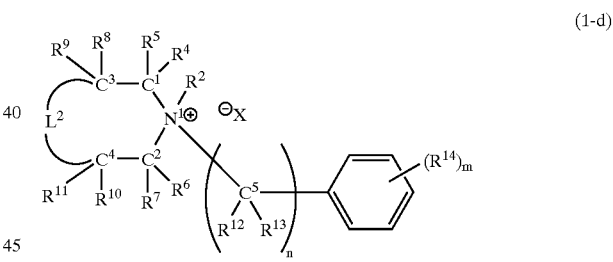

(1-d)

wherein $R^2$ represents an organic group, $R^4$ to $R^{14}$ independently represent a hydrogen atom or a substituent and $R^4$ to $R^{14}$ may bond to each other to form a ring or may bond to $L^2$ and $R^2$ to form a ring, and when the $C^3$ carbon atom and the $C^4$ carbon atom form a double bond or a triple bond in combination with the $C^1$ carbon atom and the $C^2$ carbon atom respectively, when the $C^3$ carbon atom and $C^4$ carbon atom form a double bond or a triple bond in combination with $L^2$ and when $L^2$ represents a double bond connecting the $C^3$ carbon atom with the $C^4$ carbon atom, $R^4$ to $R^{11}$ may not be present corresponding to this, n denotes 0 or a positive integer, m denotes an integer from 0 to 5, $L^2$ represents a polyvalent connecting group forming a ring containing —$C^3$—$C^1$—$N^1$—$C^2$—$C^4$— or a single bond or double bond connecting $C^3$ with $C^4$ and $X^-$ represents a conjugate base of an organic acid or inorganic acid.

10. An image forming material according to claim 1, wherein the compound represented by the general formula (1) is represented by the following general formula (1-e)

(1-e)

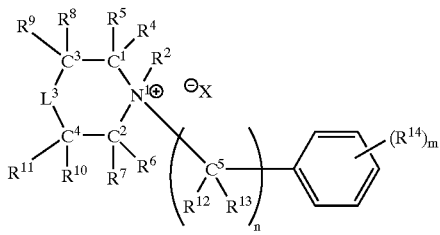

wherein $R^2$ represents an organic group, $R^4$ to $R^{14}$ independently represent a hydrogen atom or a substituent and $R^4$ to $R^{14}$ may bond to each other to form a ring or may bond to $L^3$ and/or $R^2$ to form a ring, and when the $C^3$ carbon atom and the $C^4$ carbon atom form a double bond or a triple bond in combination with the $C^1$ carbon atom and the $C^2$ carbon atom respectively, when the $C^3$ carbon atom and $C^4$ carbon atom form a double bond or a triple bond in combination with $L^3$ and when $L^3$ represents a double bond connecting the $C^3$ carbon atom with the $C^4$ carbon atom, $R^4$ to $R^{11}$ may not be present corresponding to this, m denotes an integer from 0 to 5, n denotes 0 or a positive integer, $L^3$ represents a single bond or double bond connecting $C^3$ with $C^4$ or a polyvalent connecting group which forms a ring containing —$C^3$—$C^1$—$N^1$—$C^2$—$C^4$— and is selected from —O—, —S—, —N($R^{L1}$)— and —C($R^{L2}$)($R^{L3}$)— where $R^{L1}$ to $R^{L3}$ independently represent a hydrogen atom or a substituent and may bond to $R^2$ and/or $R^4$ to $R^{14}$ to form a ring and X— represents a conjugate base of an organic acid or inorganic acid.

11. An image forming material according to claim 1, wherein the compound represented by the general formula (1) is represented by the following general formula (1-f)

(1-f)

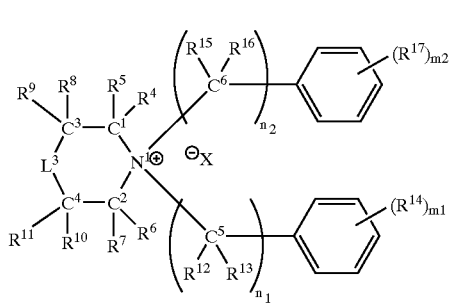

wherein $R^4$ to $R^{17}$ independently represent a hydrogen atom or a substituent and $R^4$ to $R^{17}$ may bond to each other to form a ring or may bond to $L^3$ to form a ring, and when the $C^3$ carbon atom and the $C^4$ carbon atom form a double bond or a triple bond in combination with the $C^1$ carbon atom and the $C^2$ carbon atom respectively, when the $C^3$ carbon atom and $C^4$ carbon atom form a double bond or a triple bond in combination with $L^3$ and when $L^3$ represents a double bond connecting the $C^3$ carbon atom with the $C^4$ carbon atom, $R^4$ to $R^{11}$ may not be present corresponding to this, $n^1$ and $n^2$ independently denote 0 or a positive integer, $m^1$ and $m^2$ independently denote an integer from 0 to 5, $L^3$ represents a single bond or double bond connecting $C^3$ with $C^4$ or a polyvalent connecting group which forms a ring containing —$C^3$—$C^1$—$N^1$—$C^2$—$C^4$— and is selected from —O—, —S—, —N($R^{L1}$)— and —C($R^{L2}$)($R^{L3}$)— where $R^{L1}$ to $R^{L3}$ independently represent a hydrogen atom or a substituent and may bond to $R^2$ and/or $R^4$ to $R^{14}$ to form a ring and X⁻ represents a conjugate base of an organic acid or inorganic acid.

12. An image forming material according to claim 1, wherein the compound represented by the general formula (1) is represented by the following general formula:

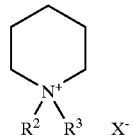

wherein $R^2$ and $R^3$ independently represent an organic group and $R^2$ and $R^3$ may bond to each other to form a ring and X⁻ represents a conjugate base of an organic acid or inorganic acid.

13. An image forming material according to claim 1, wherein the compound represented by the general formula (1) is represented by the following general formula:

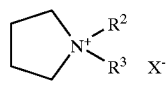

wherein $R^2$ and $R^3$ independently represent an organic group and $R^2$ and $R^3$ may bond to each other to form a ring and X⁻ represents a conjugate base of an organic acid or inorganic acid.

14. An image forming material according to claim 1, wherein the compound represented by the general formula (1) is represented by the following general formula:

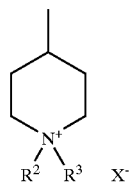

wherein $R^2$ and $R^3$ independently represent an organic group and $R^2$ and $R^3$ may bond to each other to form a ring and X⁻ represents a conjugate base of an organic acid or inorganic acid.

15. An image forming material according to claim 1, wherein the compound represented by the general formula (1) is represented by the following general formula:

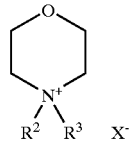

wherein $R^2$ and $R^3$ independently represent an organic group and $R^2$ and $R^3$ may bond to each other to form a ring and X⁻ represents a conjugate base of an organic acid or inorganic acid.

* * * * *